(12) United States Patent
Komatsu et al.

(10) Patent No.: US 9,322,809 B2
(45) Date of Patent: Apr. 26, 2016

(54) ELASTIC WAVE SENSOR

(71) Applicant: PANASONIC CORPORATION, Osaka (JP)

(72) Inventors: Tomoya Komatsu, Osaka (JP); Hiroyuki Nakamura, Osaka (JP); Shigeru Tsuzuki, Osaka (JP); Tomohiro Iwasaki, Shiga (JP); Tetsuo Kawasaki, Osaka (JP); Kazunori Nishimura, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 189 days.

(21) Appl. No.: 14/127,823

(22) PCT Filed: Jan. 15, 2013

(86) PCT No.: PCT/JP2013/000116
§ 371 (c)(1),
(2) Date: Dec. 19, 2013

(87) PCT Pub. No.: WO2013/108608
PCT Pub. Date: Jul. 25, 2013

(65) Prior Publication Data
US 2014/0144237 A1      May 29, 2014

(30) Foreign Application Priority Data

Jan. 20, 2012 (JP) ................................. 2012-009880
Feb. 14, 2012 (JP) ................................. 2012-029232
Feb. 15, 2012 (JP) ................................. 2012-030267

(51) Int. Cl.
*G01N 29/12* (2006.01)
*G01N 29/02* (2006.01)
*G01N 29/036* (2006.01)

(52) U.S. Cl.
CPC .............. *G01N 29/12* (2013.01); *G01N 29/022* (2013.01); *G01N 29/036* (2013.01); *G01N 2291/0255* (2013.01); *G01N 2291/0256* (2013.01); *G01N 2291/0423* (2013.01)

(58) Field of Classification Search
CPC ... G01N 29/022; G01N 29/036; G01N 29/12; G01N 2291/0255; G01N 2291/0423; G01N 2291/0256
USPC ..................................................... 73/579, 598
See application file for complete search history.

(56) References Cited

U.S. PATENT DOCUMENTS 9,124,239 B2 * 9/2015 Nakayama ........... H03H 9/0057
333/133

(Continued)

FOREIGN PATENT DOCUMENTS

DE          10113778         7/2002
GB          2390162          12/2003

(Continued)

OTHER PUBLICATIONS

International Search Report issued in International Application No. PCT/JP2013/000116 mailed Apr. 23, 2013, 1 pg.

(Continued)

*Primary Examiner* — J M Saint Surin
(74) *Attorney, Agent, or Firm* — McDermott Will & Emery LLP

(57) ABSTRACT

An acoustic wave sensor includes a piezoelectric substrate, a transmitting electrode configured to excite a main acoustic wave propagating through a propagation region of an upper surface of the piezoelectric substrate, a receiving electrode configured to receive the propagated main acoustic wave, a first insulating film provided on the propagation region of the upper surface of the piezoelectric substrate, a second insulating film provided on the upper surface of the piezoelectric substrate to cover the first insulating film, and a reaction section provided on the upper surface of the second insulating film above the propagation region. The reaction section is configured to react with an object. A velocity of a transverse wave propagating through the first insulating film is higher than a velocity of a transverse wave propagating through the second insulating film. The acoustic wave sensor described above has high detection sensitivity.

13 Claims, 23 Drawing Sheets

(56) References Cited

U.S. PATENT DOCUMENTS

| | | | |
|---|---|---|---|
| 9,136,458 B2* | 9/2015 | Komatsu | H01L 41/047 310/313 |
| 2005/0277111 A1 | 12/2005 | Itoh et al. | |
| 2008/0106354 A1* | 5/2008 | Kando | H03H 9/02228 333/193 |
| 2009/0272193 A1* | 11/2009 | Okaguchi | G01N 5/02 73/657 |
| 2011/0037344 A1 | 2/2011 | Yamane et al. | |
| 2011/0177584 A1* | 7/2011 | Kadoya | G01N 29/2443 435/287.1 |
| 2012/0146457 A1 | 6/2012 | Goto et al. | |
| 2012/0280768 A1* | 11/2012 | Nakayama | H03H 9/0057 333/193 |

FOREIGN PATENT DOCUMENTS

| | | |
|---|---|---|
| JP | 61-042891 B2 | 9/1986 |
| JP | 11-335812 A | 12/1999 |
| JP | 2005-351799 A | 12/2005 |
| JP | 2007-010378 A | 1/2007 |
| JP | 2008-122105 A | 5/2008 |
| JP | 2008-286606 A | 11/2008 |
| JP | 2009-210067 A | 9/2009 |
| WO | 2011/030519 A1 | 3/2011 |

OTHER PUBLICATIONS

The Extended European Search Report dated Nov. 27, 2015 for the related European Patent Application No. 13738781.7.

Myer Kutz et al: "Handbook of Materials Selection" In: "Handbook of Materials Selection", Jan. 1, 2002, John Wiley & Sons, Inc., New York, XP055229533, pp. 656-698.

* cited by examiner

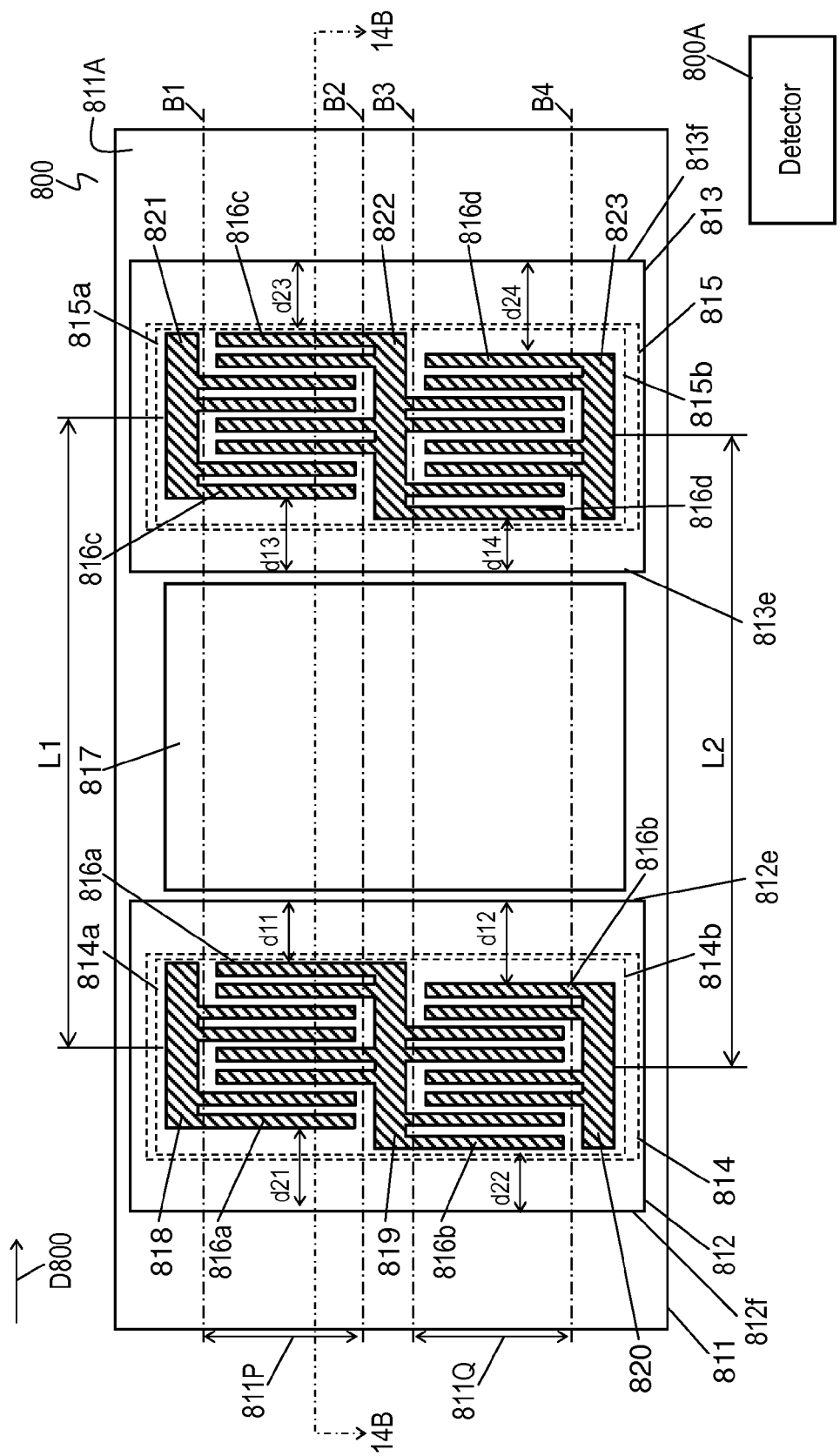

ELASTIC WAVE SENSOR

RELATED APPLICATIONS

This application is the U.S. National Phase under 35 U.S.C. §371 of International Application No. PCT/2013/000116, filed on Jan. 15, 2013, which in turn claims the benefit of Japanese Application No. 2012-009880, filed on Jan. 20, 2012, Japanese Application No. 2012-029232, filed Feb. 14, 2012 and Japanese Application No. 2012-030267, filed Feb. 15, 2012, the disclosures of which are incorporated by reference herein.

TECHNICAL FIELD

The present invention relates to an acoustic wave sensor including a reaction section configured to react with an object.

BACKGROUND ART

FIG. 20A is a schematic top view of conventional acoustic wave sensor 101. FIG. 20B is a schematic cross-sectional view of acoustic wave sensor 101 at line 20B-20B shown in FIG. 20A. Acoustic wave sensor 101 includes piezoelectric substrate 102, transmitting electrode 103 provided on piezoelectric substrate 102 for exciting a main acoustic wave, receiving electrode 104 for receiving the main acoustic wave, insulating film 105 provided on piezoelectric substrate 102 for covering transmitting electrode 103 and receiving electrode 104, and reaction section 106 provided on a propagation region on insulating film 105 and between transmitting electrode 103 and receiving electrode 104 on insulating film 105.

When a substance (such as breath or sample liquid) which may possibly contain an object to be detected is injected onto reaction section 106, the acoustic wave sensor detects a change in a propagation characteristic of an acoustic wave due to the attaching of the object, thereby detecting the presence of the object or a concentration thereof.

A conventional acoustic wave sensor similar to acoustic wave sensor 101 is described in Patent Literature 1.

FIG. 21 is a schematic cross-sectional view of another conventional acoustic wave sensor 901. Acoustic wave sensor 901 includes piezoelectric substrate 902, transmitting electrode 903 and receiving electrode 904 formed on piezoelectric substrate 902, reaction section 905 formed on a propagation path between transmitting electrode 903 and receiving electrode 904 on piezoelectric substrate 902, and a detector detecting a characteristic of a main acoustic wave excited by transmitting electrode 903.

When a substance (such as breath or inspection liquid, etc.) which may possibly contain an object to be detected is injected on reaction section 905, the detector detects a change in a frequency of an acoustic wave due to the attaching of the object, thereby allowing the acoustic wave sensor to detect the presence of the object or a concentration thereof.

A conventional acoustic wave sensor similar to acoustic wave sensor 901 is described in Patent Literature 2.

As acoustic wave sensor 901 has a smaller size, the area of reaction section 905 decreases, so that the amount of the object adsorbed on reaction section 905 reduces, accordingly deceasing detecting precision of the acoustic wave sensor 901.

The acoustic wave sensor is used to examine or analyze liquid, which is a sample, or a sample (substance to be examined) contained in liquid. The acoustic wave sensor includes a transmitting/receiving electrode portion for transmitting or receiving an acoustic wave on a piezoelectric substrate. The acoustic wave sensor utilizes a characteristic that the propagation characteristic of the acoustic wave propagating on the piezoelectric substrate changes according to the state of the surface of the piezoelectric substrate on which the acoustic wave is propagated. The acoustic wave sensors described above is used in various fields, such as medical, environmental, and food fields.

For example, a sensor including with a detection area for detecting a sample on a propagation path of an acoustic wave between transmitting/receiving electrode portions is used as a biosensor. In a general acoustic wave sensor, a metal layer is formed on the detection area. In the biosensor, an antibody layer is further formed on the metal layer. When antigen solution is injected into the antibody layer, the biosensor collects antigens by an antigen-antibody reaction. Therefore, the propagation characteristic of the acoustic wave propagating on the piezoelectric substrate is changed before and after the injection of the antigen solution. Accordingly, the amount of the collected antigens or the concentration of the antigen can be detected by detecting the change in the propagation characteristic of the acoustic wave before and after the injection of the solution.

In the acoustic wave sensor described above, the transmitting/receiving electrode portion is generally covered by a cover for preventing the transmitting/receiving electrode portion from being affected by ambient atmosphere, such as moisture, in order to prevent the deterioration in detecting sensitivity and reproducibility. The cover may be implemented by a case sealing the transmitting electrode portion and the receiving electrode portion to form a hollow space serving as a vibration area on both the electrode portions, or by a dielectric layer formed on the transmitting electrode portion and the receiving electrode portion.

FIG. 22A is a schematic top view of still another acoustic wave sensor 950. FIG. 22B is a schematic cross-sectional view of acoustic wave sensor 950 on line 22B-22B shown in FIG. 22A. In acoustic wave sensor 950, transmitting electrode portion 814 is covered and protected by transmitting electrode cover 812 while receiving electrode portion 815 is covered and protected by receiving electrode cover 813.

This type of the acoustic wave sensor is described in Patent Literature 3.

CITATION LIST

Patent Literature

Patent Literature 1: Japanese Patent Laid-Open Publication No. 2008-286606

Patent Literature 2: International Publication WO2011/030519

Patent Literature 3: Japanese Patent Laid-Open Publication No. 11-335812

SUMMARY

An acoustic wave sensor includes a piezoelectric substrate, a transmitting electrode configured to excite a main acoustic wave propagating through a propagation region of an upper surface of the piezoelectric substrate, a receiving electrode configured to receive the propagated main acoustic wave, a first insulating film provided on the propagation region of the upper surface of the piezoelectric substrate, a second insulating film provided on the upper surface of the piezoelectric substrate to cover the first insulating film, and a reaction section provided on the upper surface of the second insulating film above the propagation region. The reaction section is configured to react with an object. A velocity of a transverse wave propagating through the first insulating film is higher than a velocity of a transverse wave propagating through the second insulating film.

The acoustic wave sensor described above has high detection sensitivity.

BRIEF DESCRIPTION OF DRAWINGS

FIG. 14A is a schematic top view of an acoustic wave sensor according to Exemplary Embodiment 6.

DETAIL DESCRIPTION OF PREFERRED EMBODIMENTS

Exemplary Embodiment 1

Figure 1A:
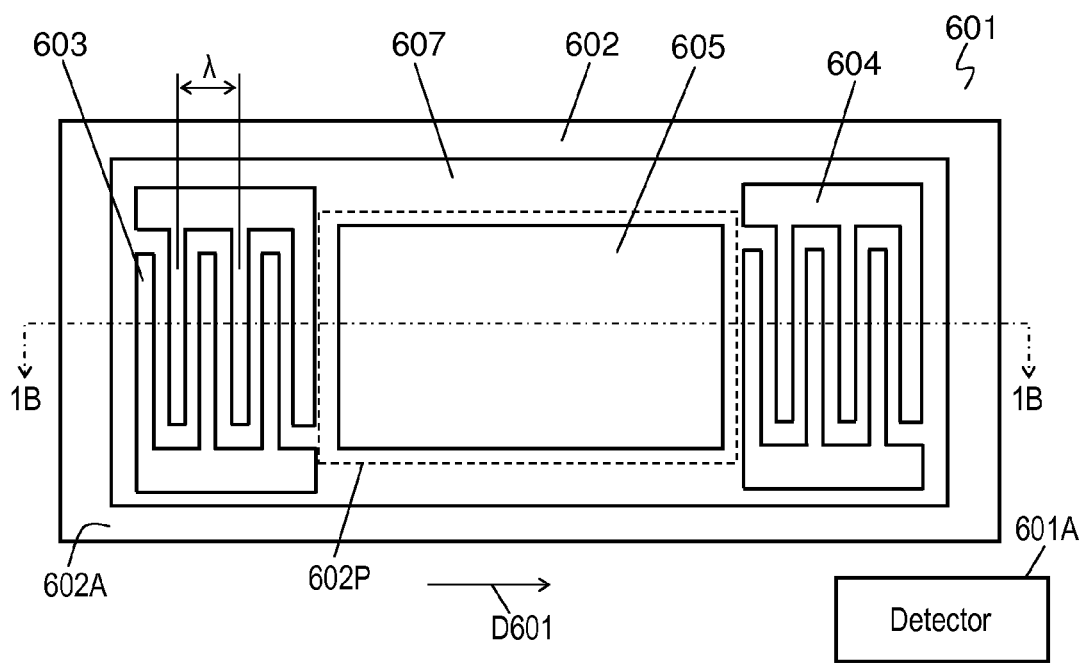
FIG. 1A is a schematic top view of an acoustic wave sensor according to Exemplary Embodiment 1.
Figure 1B:
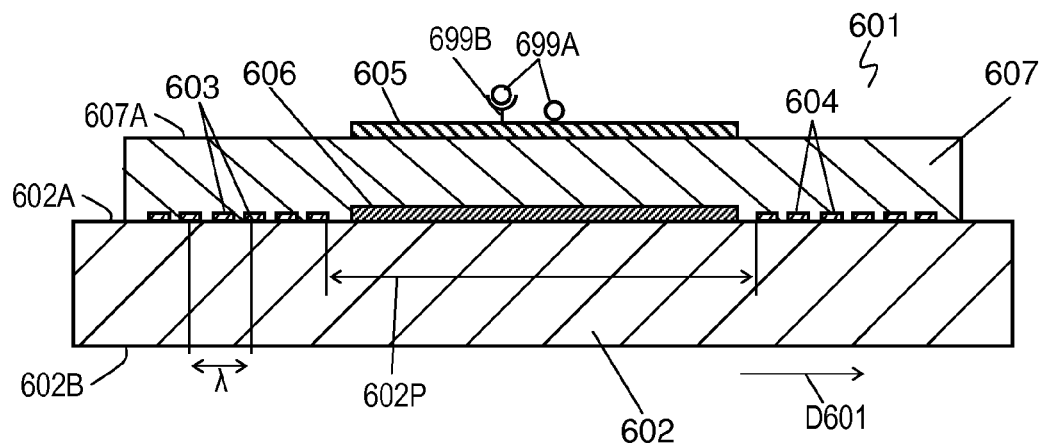
FIG. 1B is a schematic cross-sectional view of the acoustic wave sensor on line 1B-1B shown in FIG. 1A.

FIG. 1A is a schematic top view of acoustic wave sensor 601 according to Exemplary Embodiment 1. FIG. 1B is a schematic cross-sectional view of acoustic wave sensor 601 on line 1B-1B shown in FIG. 1A. Acoustic wave sensor 601 is a biosensor employing a transversal type acoustic wave element, and detects an object, such as protein, gene, or signal molecule, based upon a molecule recognition mechanism of a biological body.

Acoustic wave sensor 601 includes piezoelectric substrate 602, transmitting electrode 603 provided on upper surface 602A of piezoelectric substrate 602, receiving electrode 604 provided on upper surface 602A of piezoelectric substrate 602, insulating film 606 provided on upper surface 602A of piezoelectric substrate 602, insulating film 607 provided on upper surface 602A of piezoelectric substrate 602, and reaction section 605 provided on upper surface 607A of insulating film 607. Transmitting electrode 603 is configured to excite a main acoustic wave, such as a Shear-Horizontal (SH) wave, a Shear-Vertical (SV) wave, a Rayleigh wave, or a Love wave. Receiving electrode 604 is configured to receive the excited main acoustic wave. The exited main acoustic wave propagates through propagation region 602P between transmitting electrode 603 and receiving electrode 604 on upper surface 602A of piezoelectric substrate 602 in propagation direction D601 directed from transmitting electrode 603 to receiving electrode 604. Insulating film 606 is provided on propagation region 602P of upper surface 602A of piezoelectric substrate 602. Insulating film 607 covers transmitting electrode 603, receiving electrode 604, and insulating film 606. Reaction section 605 is provided above propagation region 602P. Reaction section 605 is configured to react with object 699A. Specifically, reaction section 605 is configured to be bound to object 699A, or to be bound to binding substance 699B binding with object 699A, or to react with object 699A, or to react with binding substance 699B binding with object 699A. A characteristic (phase characteristic, or frequency characteristic) of the main acoustic wave received by receiving electrode 604 is detected by detector 601A. Reaction section 605 and insulating film 606 have the same area and coincide with each other in view from above.

Acoustic wave sensor 601 is mounted on a mother board installed in various medical devices. Acoustic wave sensor 601 can be mounted face down on the mother board with upper surface 602A of piezoelectric substrate 602 facing the mother board. In this case, electrodes 603 and 604 are electrically connected to detector 601A via metal bumps. Acoustic wave sensor 601 may be mounted face up on lower surface 602B of piezoelectric substrate 602 being bonded to the mother board. In this case, electrodes 603 and 604 are electrically connected to detector 601A via metal wires.

In acoustic wave sensor 601 according to Embodiment 1, detector 601A detects the frequency change or the phase change of the main acoustic wave received by receiving electrode 604. However, detector 601A may detect the change in the other characteristics, such as a velocity, amplitude, or wavelength, of the main acoustic wave.

When substance (breath, inspection liquid, etc.) possibly containing object 699A is injected on reaction section 605, the mass of reaction section 605 is changed due to the attaching of object 699A. Detector 601A detects the characteristic change of the main acoustic wave by detecting the change in the mass of reaction section 605, thereby detecting the presence of object 699A or the concentration of object 699A.

Figure 20A:
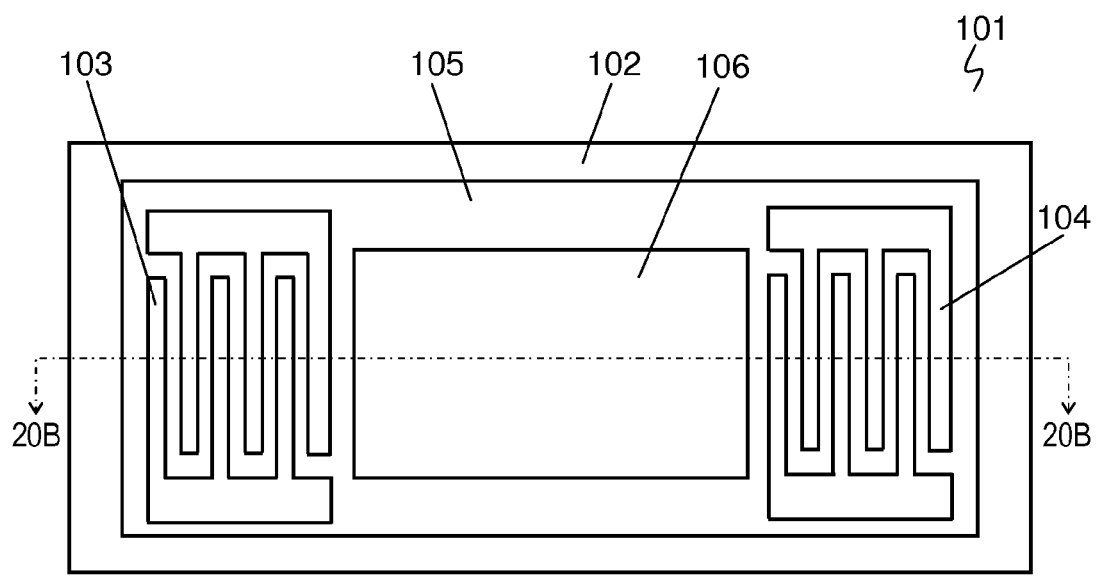
FIG. 20A is a schematic top view of a conventional acoustic wave sensor.
Figure 20B:
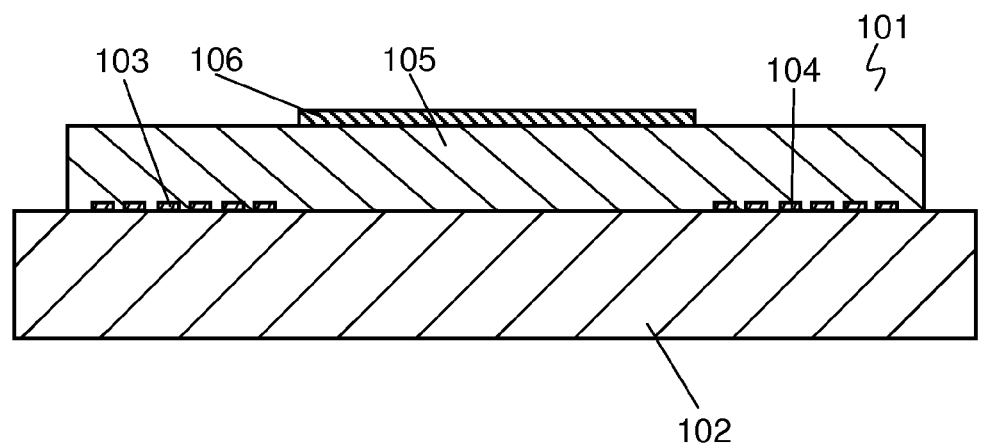
FIG. 20B is a schematic cross-sectional view of the acoustic wave sensor on line 20B-20B shown in FIG. 20A.
Figure 21:
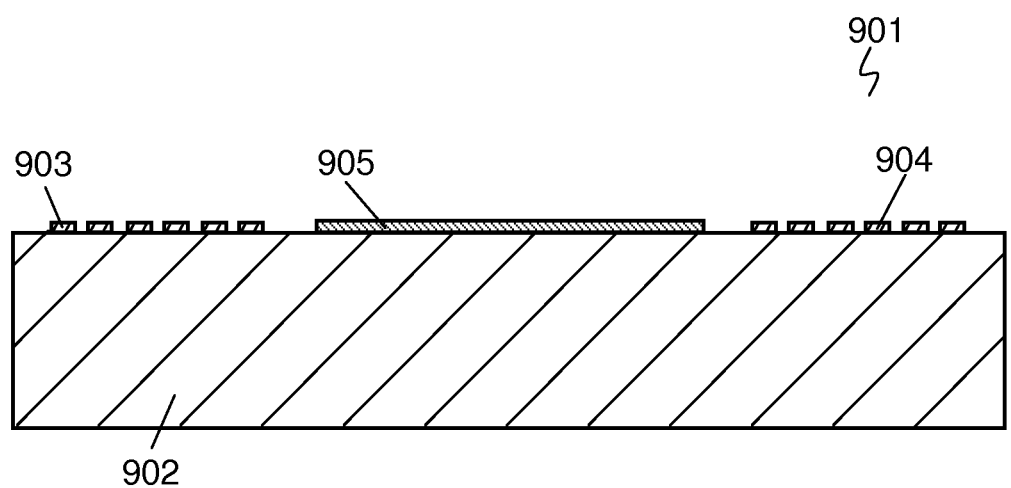
FIG. 21 is a schematic cross-sectional view of another conventional acoustic wave sensor.

In conventional acoustic wave sensor 101 shown in FIGS. 20A and 20B, acoustic wave energy leaks into piezoelectric substrate 102 as a bulk wave in the propagation region, so that the main acoustic wave may not concentrate near the surface of reaction section 106, accordingly, deteriorating the detection sensitivity. The main acoustic wave can concentrate near the surface of reaction section 106 by decreasing the velocity of the main acoustic wave depending on the material and thickness of reaction section 106. However, when the velocity of the main acoustic wave propagating through the vicinity of the surface of reaction section 106 is excessively decreased, the change in the propagation characteristic of the main acoustic wave caused by the attaching of the object becomes small, hence deteriorating the detection sensitivity.

In acoustic wave sensor 601 according to Embodiment 1 shown in FIGS. 1A and 1B, the velocity of the transverse wave propagating through insulating film 606 is higher than the speed of the transverse wave propagating through insulating film 607. Since the energy of the acoustic wave concentrates on a medium with a low velocity, insulating film 606 with a high velocity has a function of concentrating the main acoustic wave on the vicinity of the surface of reaction section 605. In addition, since the velocity of the main acoustic wave propagating around the surface of reaction section 605 becomes higher due to the influence of insulating film 606, hence canceling the reduction in the velocity of the main acoustic wave caused by the formation of reaction section 605. These effects can increase the change in the propagation characteristic of the main acoustic wave, the change being caused when object 699A is attached onto reaction section 605, or when object 699A is bound to binding substance 699B. Accordingly, the detection sensitivity of acoustic wave sensor 601 can be enhanced.

Insulating film 606 having a higher velocity than insulating film 607 is provided between reaction section 605 and piezoelectric substrate 602, and prevents acoustic wave energy from leaking to piezoelectric substrate 602 without decreasing the velocity of the main acoustic wave on reaction section 605. This can increase the change in the propagation characteristic of the main acoustic wave when the substance (such as breath or sample liquid) possibly containing the object is injected, thus enhancing the detection sensitivity of the acoustic wave sensor 601.

The configuration of acoustic wave sensor 601 will be detailed below.

Piezoelectric substrate 602 is made of a piezoelectric single crystal substrate. For example, piezoelectric substrate 602 is made of a piezoelectric single crystal substrate of quartz, langasite-based, lithium niobate-based, lithium tantalate-based, or potassium niobate-based. Piezoelectric substrate 602 made of lithium niobate exhibits small loss characteristic, increasing the detection sensitivity of acoustic wave sensor 601.

Each of electrodes 603 and 604 is an interdigital transducer (IDT) electrode including a pair of comb-shaped electrodes. The comb-shaped electrode includes a bus bar and plural electrode fingers extending from the bus bar. Each of electrodes 603 and 604 is arranged such that the electrode fingers of one comb-shaped electrode interdigitate with the plural electrode fingers of the other comb-shaped electrode. The plural electrode fingers of one comb-shaped electrode are arranged at pitch $\lambda$. The thicknesses of electrodes 603 and 604 range from about $0.005\lambda$ to $0.2\lambda$. Each of electrodes 603 and 604 is made of a single metal of aluminum, copper, silver, gold, platinum, titanium, tungsten, molybdenum, or chrome, or an alloy mainly containing these metals, or has a laminated structure of these metals. Electrodes 603 and 604 made of metal, such as gold, platinum, or tungsten, having a high density can prevent the acoustic wave energy from leaking into piezoelectric substrate 602. In other words, electrodes 603 and 604 described above exhibit low-loss characteristic, thereby enhancing the detection sensitivity of acoustic wave sensor 601.

The velocity of the transverse wave propagating through insulating film 606 is preferably higher than the velocity of the slowest transverse wave propagating through piezoelectric substrate 602. This configuration can effectively prevent the leakage of the main acoustic wave into piezoelectric substrate 602. Insulating film 606 may be made of silicon nitride (SiN), silicon oxynitride (SiON), silicon oxide ($SiO_2$), aluminum nitride (AlN), aluminum oxide ($Al_2O_3$), diamond (C), or silicon (Si). Insulating film 606 made of silicon nitride (SiN) may have a thickness ranging from about $0.01\lambda$ to $0.2\lambda$. Insulating film 606 made of aluminum nitride (AlN) or silicon nitride (SiN) allows the velocity of the transverse wave propagating through insulating film 606 to be higher, and effectively prevents the main acoustic wave from leaking into piezoelectric substrate 602, thus enhancing the detection sensitivity of acoustic wave sensor 601.

Insulating film 607 is preferably made of a medium allowing the velocity of the transverse wave propagating through insulating film 607 to be lower than the velocity of the slowest transverse wave propagating through piezoelectric substrate 602. This configuration causes the main acoustic wave to concentrate on the vicinity of the surface of reaction section 605. For example, silicon oxide ($SiO_2$), tantalum oxide ($Ta_2O_5$), or tellurium oxide ($TeO_3$) is used for insulating film 607. Insulating film 607 made of silicon oxide ($SiO_2$) may have a thickness ranging from about $0.05\lambda$ to $0.3\lambda$. Insulating film 607 particularly made of tantalum oxide ($Ta_2O_5$) allows the velocity of the transverse wave propagating through insulating film 607 to become low, accordingly allowing the main acoustic wave to concentrate on the vicinity of reaction section 605. Insulating film 607 is provided on at least propagation region 602P. Insulating film 607 made of a material, such as silicon oxide (SiO2), having a frequency-temperature coefficient reverse to that of piezoelectric substrate 602 covers electrodes 603 and 604, thereby improving a frequency-temperature characteristic of acoustic wave sensor 601.

Reaction section 605 is made of an appropriate antibody that can be bound to or reacts with object 699A possibly contained in breath, or binding substance 699B binding with object 699A. The antibody is fixed on upper surface 607A of insulating film 607 with an adhesive layer made of an organic film or a metal layer made of a single metal or an alloy of nickel, copper, gold, cobalt, or zinc. Gold, which has high corrosion resistance and high density, is particularly preferable for the material of the adhesive layer. The antibody may be fixed directly on insulating film 607 without the adhesive layer.

According to Embodiment 1, reaction section 605 is located above propagation region 602P. Reaction section 605 may located within a range where energy of the main acoustic wave reaches, or is not necessarily located between electrodes 603 and 604.

Exemplary Embodiment 2

Figure 2A:
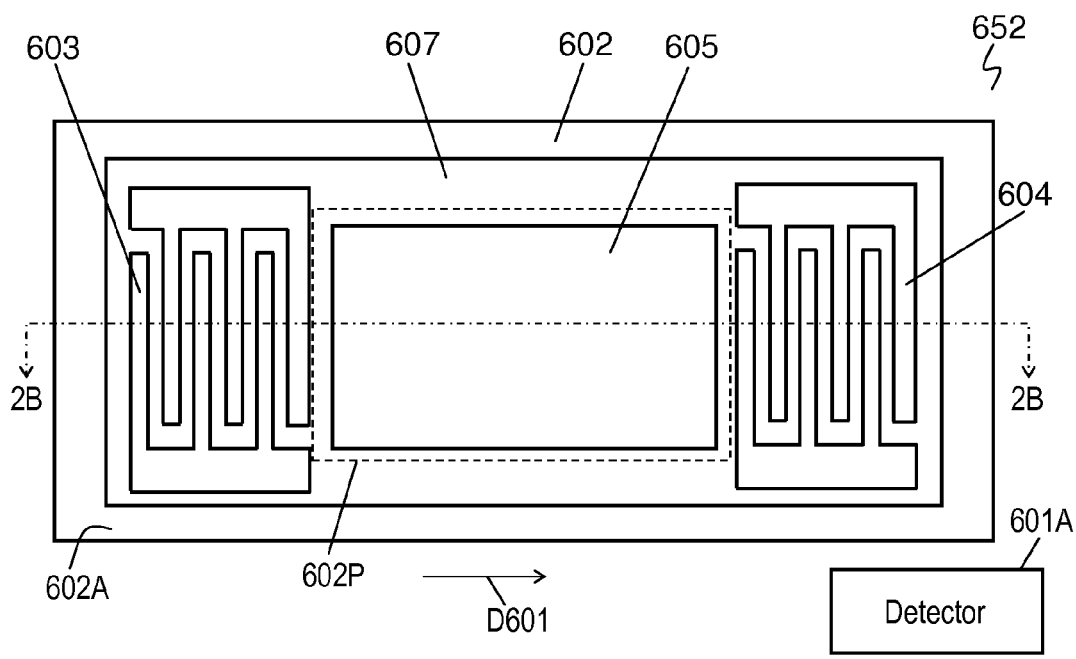
FIG. 2A is a schematic top view of an acoustic wave sensor according to Exemplary Embodiment 2.
Figure 2B:
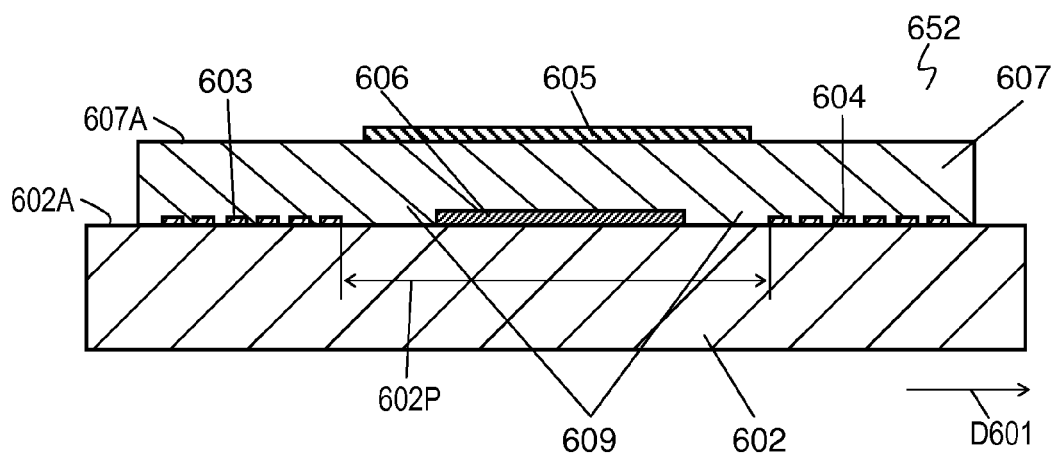
FIG. 2B is a schematic cross-sectional view of the acoustic wave sensor on line 2B-2B shown in FIG. 2A.

FIG. 2A is a schematic top view of acoustic wave sensor 652 according to exemplary Embodiment 2. FIG. 2B is a schematic cross-sectional view of acoustic wave sensor 652 on line 2B-2B shown in FIG. 2A. In FIGS. 2A and 2B, components identical to those of acoustic wave sensor 601 according to Embodiment 1 shown in FIGS. 1A and 1B are denoted by the same reference numerals.

As shown in FIGS. 2A and 2B, in acoustic wave sensor 652 according to Embodiment 2, edges of insulating film 606 are apart from the ends of reaction section 605 and are located in reaction section 605 in propagation direction D601 in view from above upper surface 602A of piezoelectric substrate 602. Insulating film 607 has transition region 609 that is located directly below reaction section 605 and is not located directly above insulating film 606. The main acoustic wave can move to the vicinity of the surface of reaction section 605 in transition region 609. Therefore, acoustic wave sensor 652 can prevent the reflection of the main acoustic wave at the edges of insulating film 606 more than acoustic wave sensor 601 according to Embodiment 1, efficiently allowing the main acoustic wave to concentrate on the vicinity of the surface of reaction section 605.

Exemplary Embodiment 3

Figure 3A:
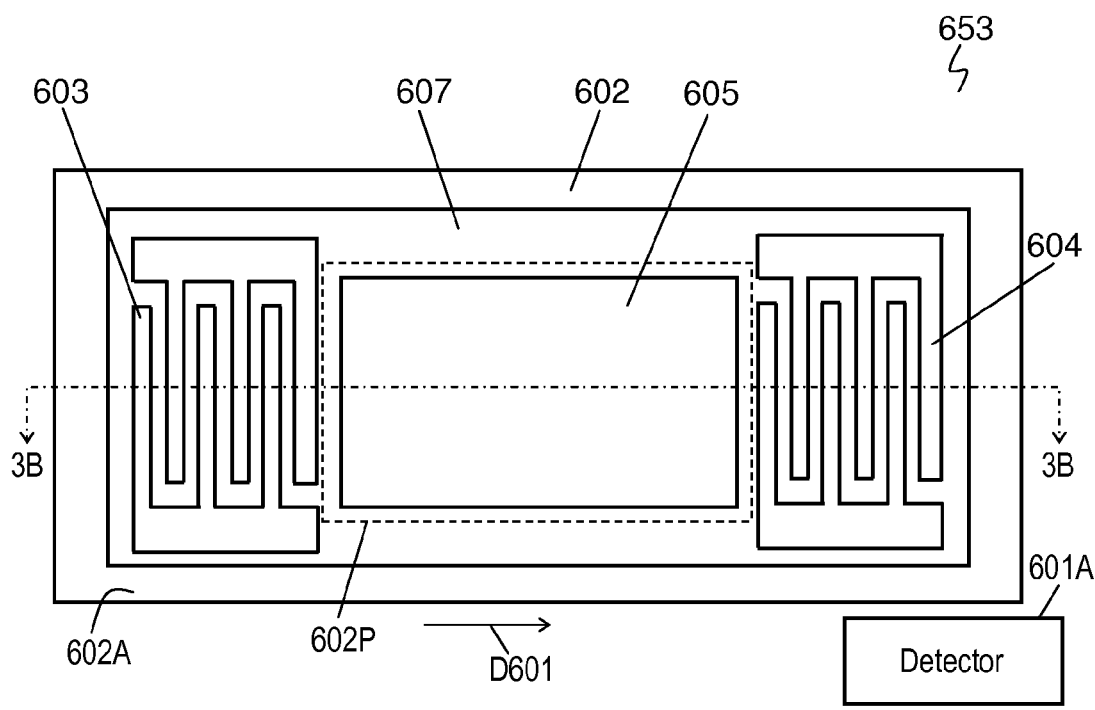
FIG. 3A is a schematic top view of an acoustic wave sensor according to Exemplary Embodiment 3.
Figure 3B:
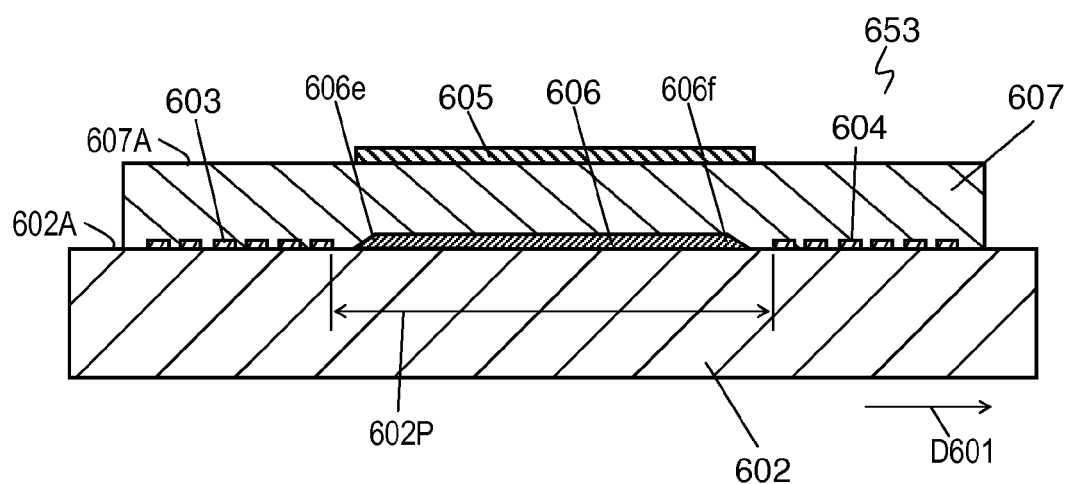
FIG. 3B is a schematic cross-sectional view of the acoustic wave sensor on line 3B-3B shown in FIG. 3A.

FIG. 3A is a schematic top view of acoustic wave sensor 653 according to Exemplary Embodiment 3. FIG. 3B is a schematic cross-sectional view of acoustic wave sensor 653 on line 3B-3B shown in FIG. 3A. In FIGS. 3A and 3B, components identical to those of acoustic wave sensor 601 according to Embodiment 1 shown in FIGS. 1A and 1B are denoted by the same reference numerals.

In acoustic wave sensor 653 according to Embodiment 3, each of ends 606e and 606f of insulating film 606 facing electrodes 603 and 604 has a tapered shape having a thickness of insulating film 606 decreasing from the center part toward electrodes 603 and 604, as shown in FIGS. 3A and 3B. This configuration can prevent the velocity of the main acoustic wave from rapidly changing at the ends of reaction section 605. Therefore, acoustic wave sensor 653 can prevent the reflection of the main acoustic wave at the edges of insulating film 606 more than acoustic wave sensor 601 according to Embodiment 1, efficiently allowing the main acoustic wave to concentrate on the vicinity of the surface of reaction section 605.

Exemplary Embodiment 4

Figure 4:
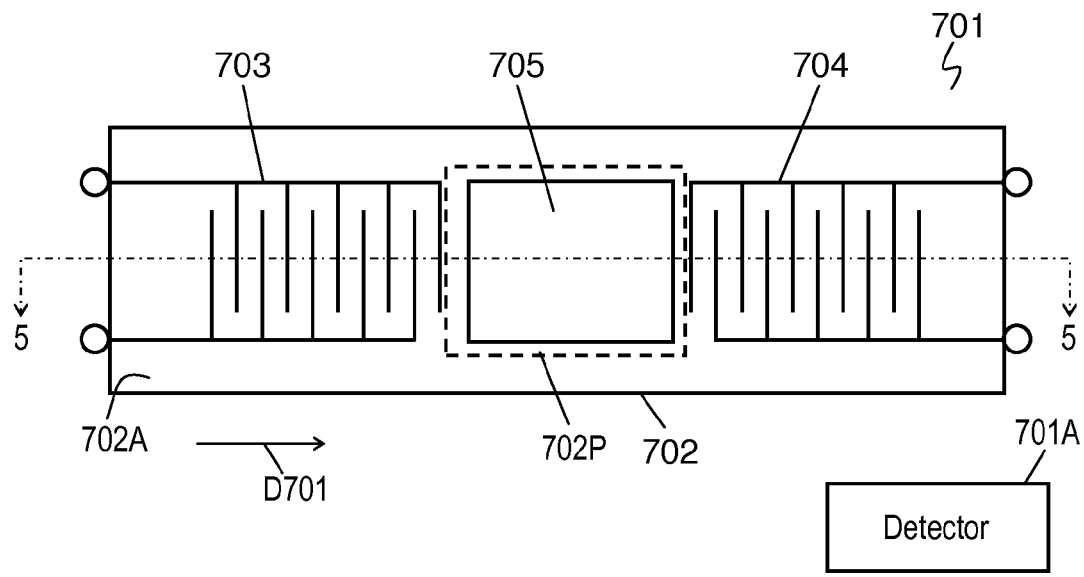
FIG. 4 is a schematic top view of an acoustic wave sensor according to Exemplary Embodiment 4.
Figure 5:
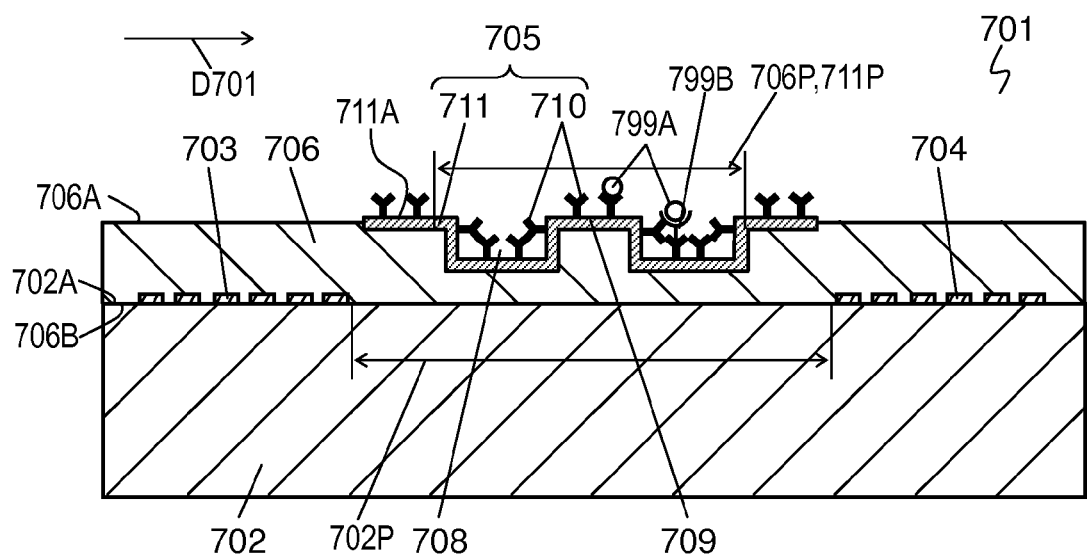
FIG. 5 is a schematic cross-sectional view of the acoustic wave sensor on line 5-5 shown in FIG. 4.

FIG. 4 is a schematic top view of acoustic wave sensor 701 according to Exemplary Embodiment 4. FIG. 5 is a schematic cross-sectional view of acoustic wave sensor 701 on line 5-5 shown in FIG. 4. Acoustic wave sensor 701 is a biosensor employing a transversal type acoustic wave element, and detects an object, such as protein, gene, or signal molecule, based upon a molecule recognition mechanism of a biological body.

Acoustic wave sensor 701 includes piezoelectric substrate 702, transmitting electrode 703 provided on upper surface 702A of piezoelectric substrate 702, receiving electrode 704 provided on upper surface 702A of piezoelectric substrate 702, dielectric film 706 provided on upper surface 702A of piezoelectric substrate 702, and reaction section 705 provided on upper surface 706A of dielectric film 706. Transmitting electrode 703 is configured to excite a main acoustic wave. Receiving electrode 704 is configured to receive the excited main acoustic wave. The exited main acoustic wave propagates through propagation region 702P on upper surface 702A of piezoelectric substrate 702 between transmitting electrode 703 and receiving electrode 704 in propagation direction D701 directed from transmitting electrode 703 to receiving electrode 704. Dielectric film 706 is provided on propagation region 702P of upper surface 702A of piezoelectric substrate 702. Reaction section 705 is provided above propagation region 702P. Reaction section 705 is configured to react with object 799A. Specifically, reaction section 705 is configured to be bound to object 799A, or binding substance 799B binding with object 799A, or to react with object 799A or binding substance 799B binding with object 799A. A characteristic (phase characteristic, or frequency characteristic) of the main acoustic wave received by receiving electrode 704 is detected by detector 701A. Upper surface 706A of dielectric film 706 has corrugate portion 706P having grooves 708 and ridges 709. Since reaction section 705 is bonded to upper surface 706A of dielectric film 706, upper surface 711A of adhesive layer 711 forming reaction section 705 has corrugate portion 711P having ridges and grooves. Corrugate portion 706P on upper surface 706A of dielectric film 706 is located below corrugate portion 711P on upper surface 711A of adhesive layer 711. Lower surface 706B of dielectric film 706 is located on upper surface 702A of piezoelectric substrate 702.

Acoustic wave sensor 701 is mounted on a mother board installed into various medical devices. Acoustic wave sensor 701 can be mounted face down onto the mother board with upper surface 702A of piezoelectric substrate 702 facing the mother board. In this case, electrodes 703 and 704 are electrically connected to detector 701A via metal bumps. Acoustic wave sensor 701 may be mounted face up with lower surface 702B of piezoelectric substrate 702 being bonded to the mother board. In this case, electrodes 703 and 704 are electrically connected to detector 701A via metal wires.

In acoustic wave sensor 701 according to Embodiment 4, detector 701A detects the frequency change or the phase change of the main acoustic wave received by receiving electrode 704. However, detector 701A may detect the change in the other characteristics, such as a velocity, amplitude, or wavelength, of the main acoustic wave.

When substance (such as breath or sample liquid) possibly containing object 799A is injected on reaction section 705, the mass of reaction section 705 is changed due to the attaching of object 799A. Detector 701A detects the characteristic change of the main acoustic wave by the change in the mass of reaction section 705, thereby detecting the presence of object 799A or a concentration of object 799A.

In acoustic wave sensor 701, adhesive layer 711 forming reaction section 705 is formed on groove 708 or ridge 709 on upper surface 706A of dielectric film 706, hence having a large surface area so that the amount of the object or the amount of the binding substance, adsorbed on reaction section 705, increases to enhance the detecting precision of acoustic wave sensor 701.

The configuration of acoustic wave sensor 701 will be detailed below.

Piezoelectric substrate 702 is made of a piezoelectric single crystal substrate. For example, piezoelectric substrate 702 is made of a piezoelectric single crystal substrate of quartz, langasite-based, lithium niobate-based, lithium tantalate-based, or potassium niobate-based. Piezoelectric substrate 702 made of lithium niobate particularly exhibits low-loss characteristic, hence enhancing the detection sensitivity of acoustic wave sensor 701.

Each of electrodes 703 and 704 is an interdigital transducer (IDT) electrode including a pair of comb-shaped electrodes. Each comb-shaped electrode includes a bus bar and plural electrode fingers extending from the bus bar. Electrodes 703 and 704 are arranged such that the plural electrode fingers of one comb-shaped electrode interdigitate with the plural electrode fingers of the other comb-shaped electrode. Transmitting electrode 703 is configured to excite a main acoustic wave, such as a Shear-Horizontal (SH) wave or a Rayleigh wave while receiving electrode 704 is configured to receive the excited main acoustic wave. Each of electrodes 703 and 704 is made of a single metal of aluminum, copper, silver, gold, platinum, titanium, tungsten, molybdenum, or chrome, or an alloy mainly containing these metals, or has a laminated structure of these metals.

Reaction section 705 is formed such that antibody 710 which is a reaction substance reacting with the object possibly contained in breath, or the binding substance binding with the object, is bound onto upper surface 706A of dielectric film 706. Antibody 710 is fixed onto dielectric film 706 with adhesive layer 711 made of a metal or an organic substance. Antibody 710 may be fixed directly on dielectric film 706 without adhesive layer 711. According to Embodiment 4, reaction section 705 is located above propagation region 702P. Reaction section 705 may be located within a range which energy of the main acoustic wave reaches. Thus, reaction section 705 is not necessarily located between electrodes 703 and 704.

Dielectric film 706 is provided at least above propagation region 702P having the main acoustic wave propagating therein. Dielectric film 706 is made of a material, such as silicon oxide ($SiO_2$), having a frequency-temperature coefficient reverse to that of piezoelectric substrate 702. Dielectric film 706 covering electrodes 703 and 704 enhances frequency-temperature characteristic of acoustic wave sensor 701. Dielectric film 706 may be made of other dielectric substance, such as silicon nitride, silicon oxynitride, aluminum nitride, aluminum oxide, tantalum oxide, tellurium oxide, diamond, or silicon.

Groove 708 or ridge 709 on the upper surface of dielectric film 706 is formed in a process for fabricating dielectric film 706 on upper surface 702A of piezoelectric substrate 702 by sputtering or vapor deposition, and then, a predetermined area on dielectric film 706 is etched by dry etching.

Figure 6:
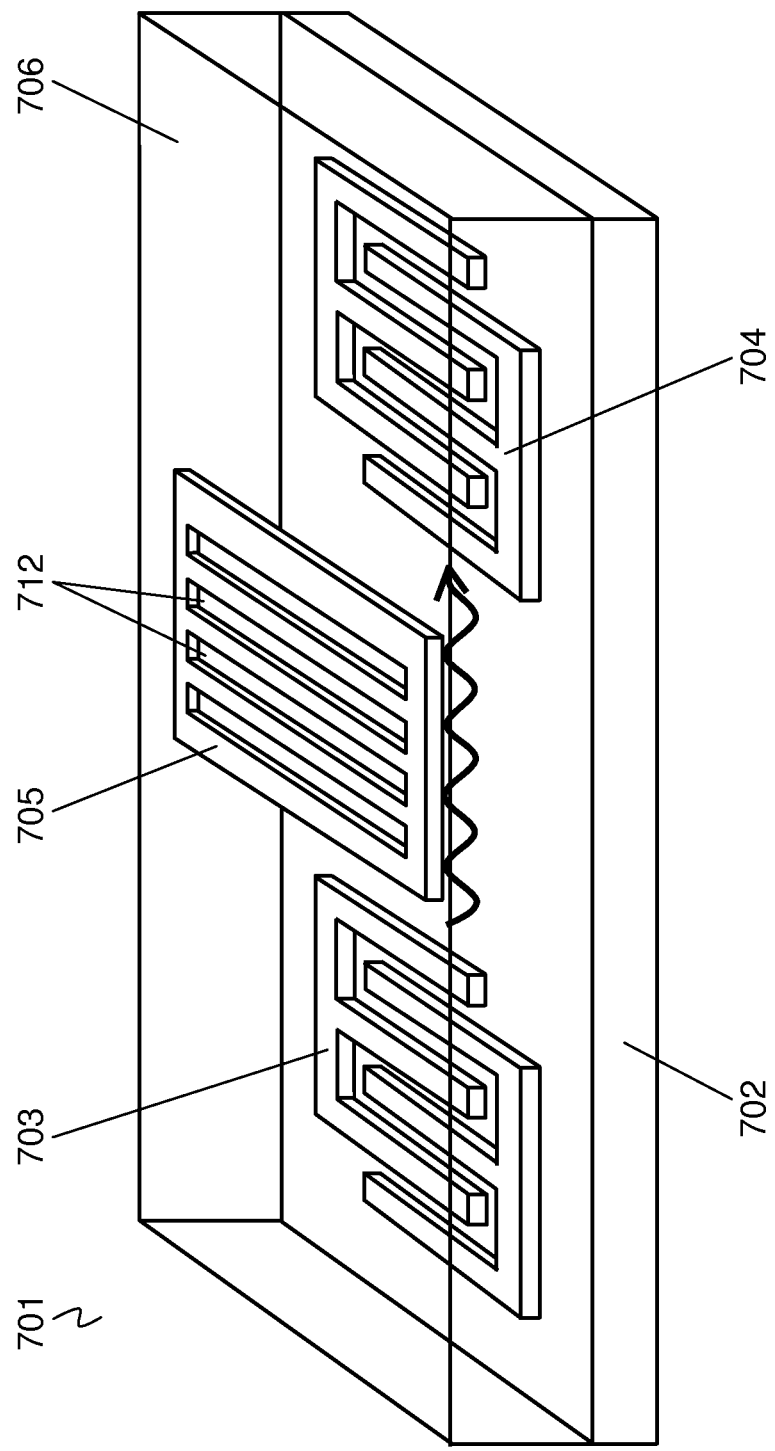
FIG. 6 is a schematic perspective view of the acoustic wave sensor according to Embodiment 4.
Figure 7:
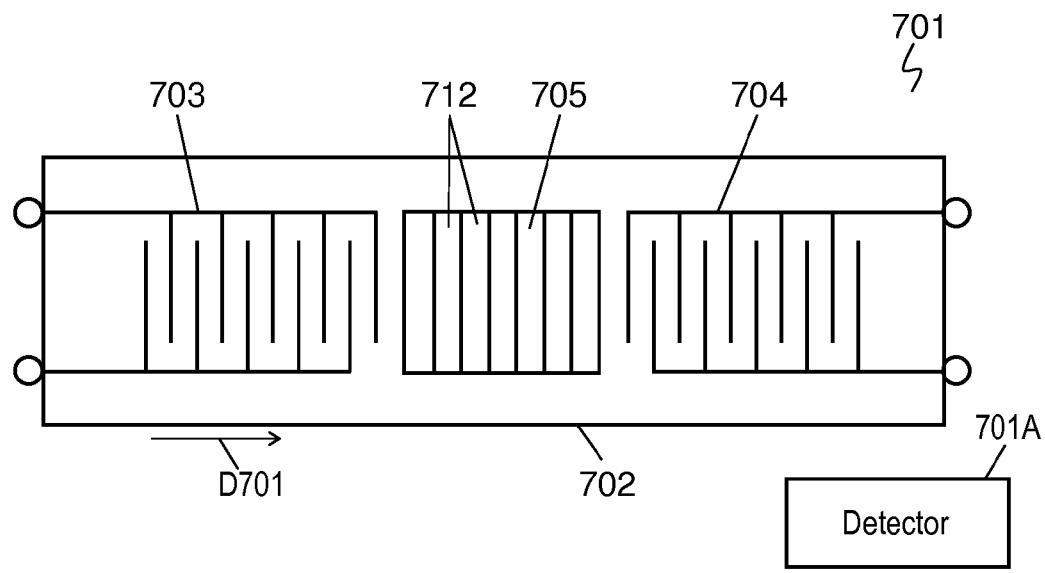
FIG. 7 is a schematic top view of the acoustic wave sensor according to Embodiment 4.

FIGS. 6 and 7 are a schematic perspective view and a schematic top view of acoustic wave sensor 701, respectively. Groove 708 of corrugate portion 711P is constituted by slit 712. In this case, slit 712 extends perpendicularly to propagation direction D701 of the main acoustic wave. This configuration reduces the propagation loss of the main acoustic wave. The width of slit 712 in propagation direction D701 may be larger than the maximum width of antibody 710 on reaction section 705. This configuration allows antibody 710 to be fixed in slit 712.

As illustrated in FIGS. 6 and 7, plural slits 712 are arranged in propagation direction D701 at a predetermined pitch. This pitch is different from a value n·λ/2 defined by integer n and wavelength λ of the acoustic wave on propagation region 702P. This configuration prevents noise superposition caused by the reflection of unnecessary wave on plural slits 712. The pitch of slits 712 in propagation direction D701 of the main acoustic wave is preferably determined to be λ/4+n·λ/2. This configuration can prevent the noise superposition caused by the reflection of unnecessary wave on plural slits 712.

Figure 8:
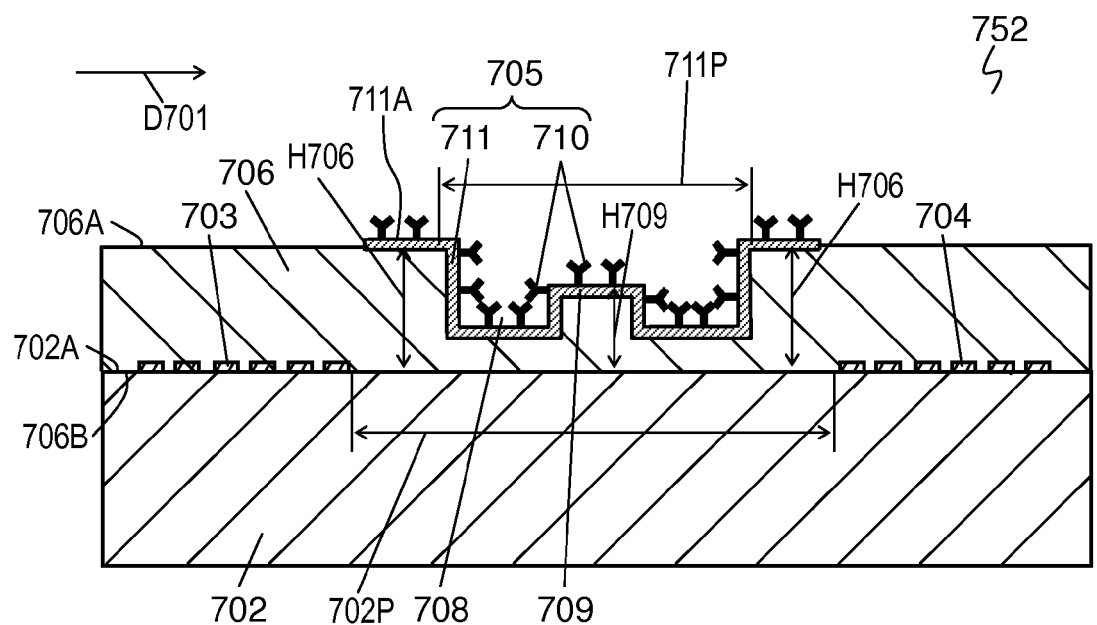
FIG. 8 is a schematic cross-sectional view of another acoustic wave sensor according to Embodiment 4.

FIG. 8 is a schematic cross-sectional view of another acoustic wave sensor 752 according to Embodiment 4. In FIG. 8, components identical to those of acoustic wave sensor 701 shown in FIGS. 4 to 7 are denoted by the same reference numerals. In acoustic wave sensor 752 shown in FIG. 8, an average thickness of a portion of dielectric film 706 where reaction section 705 is formed is smaller than the average thickness of a portion of dielectric film 706 other than reaction section 705. Thickness H709 from lower surface 706B of dielectric film 706, i.e., from upper surface 702A of piezoelectric substrate 702, to upper surface 706A of dielectric film 706 on ridge 709 of corrugate portion 711P is smaller than thickness H706 from lower surface 706B of dielectric film 706, i.e., from upper surface 702A of piezoelectric substrate 702, to upper surface 706A of dielectric film 706 around corrugate portion 711P. This configuration allows reaction section 705 to function as a flow channel having the sample liquid flowing therein.

Figure 9:
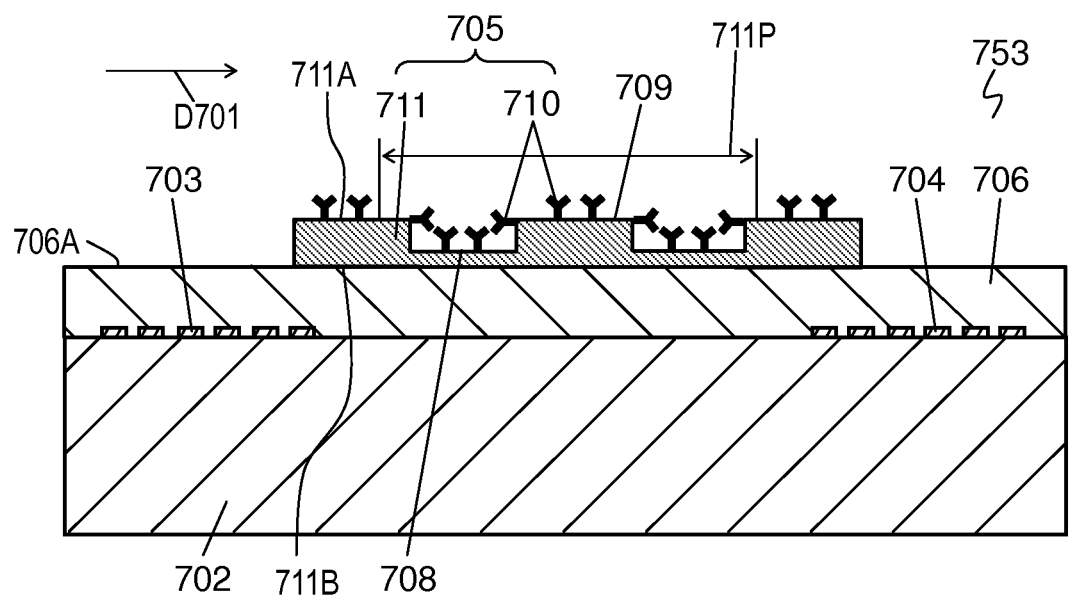
FIG. 9 is a schematic cross-sectional view of still another acoustic wave sensor according to Embodiment 4.

FIG. 9 is a schematic cross-sectional view of still another acoustic wave sensor 753 according to Embodiment 4. In FIG. 9, components identical to those of acoustic wave sensor 701 shown in FIGS. 4 to 7 are denoted by the same reference numerals. In acoustic wave sensor 753 shown in FIG. 9, upper surface 706A of dielectric film 706 and lower surface 711B of adhesive layer 711 including corrugate portion 711P are flat, and corrugate portion 711P having groove 708 and ridge 709 is formed on upper surface 711A of adhesive layer 711 by locally changing the thickness of adhesive layer 711. Groove 708 or ridge 709 on upper surface 711A of adhesive layer 711 is formed by a process for fabricating adhesive layer 711 on dielectric film 706 by sputtering or vapor deposition, and then, adhesive layer 711 is etched into a predetermined shape by dry etching.

Corrugate portion 711P having groove 708 or ridge 709 formed on upper surface 711A of adhesive layer 711 of reaction section 705 increases the surface area of upper surface 711A of adhesive layer 711. This configuration increases the amount of the object or the amount of the binding substance, adsorbed on reaction section 705, accordingly enhancing the detecting precision of acoustic wave sensor 753.

Exemplary Embodiment 5

Figure 10:
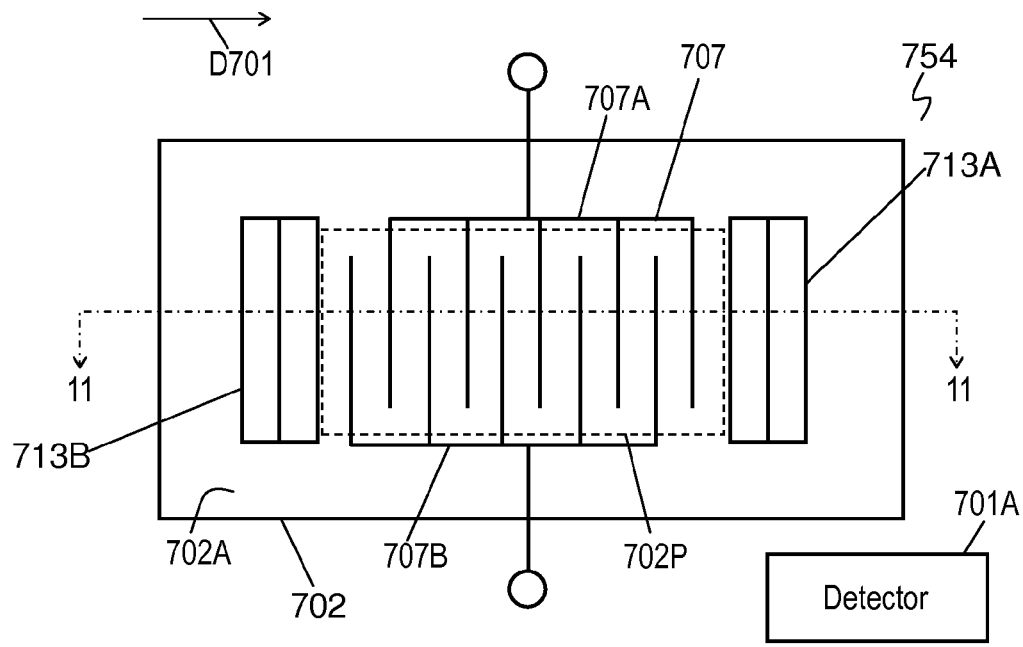
FIG. 10 is a schematic top view of an acoustic wave sensor according to Exemplary Embodiment 5.
Figure 11:
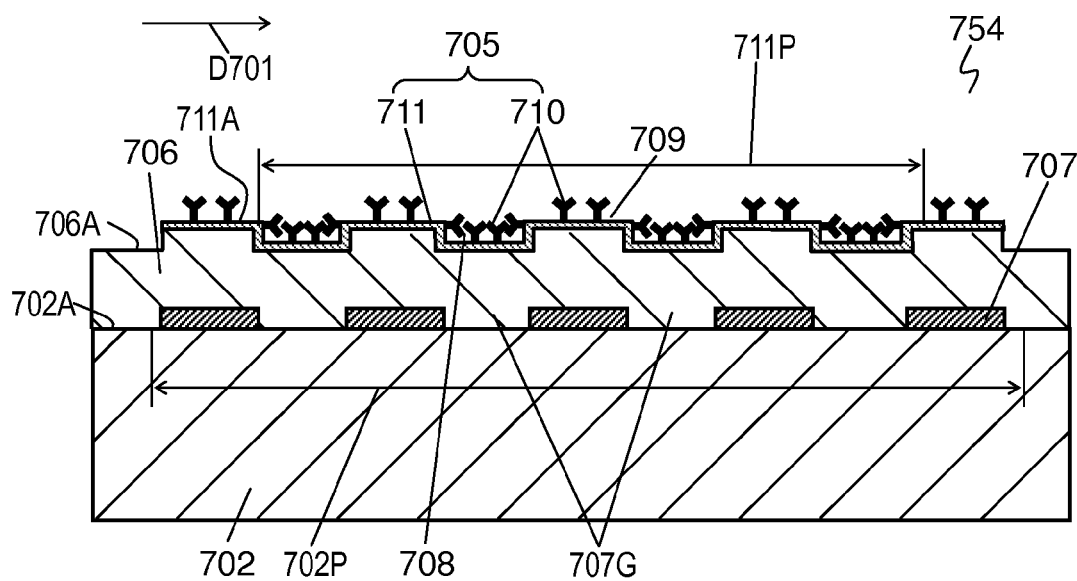
FIG. 11 is a schematic cross-sectional view of the acoustic wave sensor on line 11-11 shown in FIG. 10.

FIG. 10 is a schematic top view of acoustic wave sensor 754 according to exemplary Embodiment 5. FIG. 11 is a schematic cross-sectional view of acoustic wave sensor 754 on line 11-11 shown in FIG. 10. In FIGS. 10 and 11, components identical to those of acoustic wave sensor 701 shown in FIGS. 4 to 7 are denoted by the same reference numerals.

Acoustic wave sensor 754 shown in FIGS. 10 and 11 is a biosensor employing an acoustic wave element of a one-port resonator, and detects an object, such as protein, gene, or signal molecule, based upon a molecule recognition mechanism of a biological body.

Acoustic wave sensor 754 includes piezoelectric substrate 702 and electrode 707 provided on upper surface 702A of piezoelectric substrate 702. Electrode 707 is configured to excite a main acoustic wave propagating through upper surface 702A of piezoelectric substrate 702 in propagation direction D701 and receive the propagated main acoustic wave. Electrode 707 is an interdigital transducer (IDT) electrode including a pair of comb-shaped electrodes 707A and 707B. Each of comb-shaped electrodes 707A and 707B includes a bus bar and plural electrode fingers extending from the bus bar. Electrode 707 is arranged such that the plural electrode fingers of one comb-shaped electrode interdigitate with the plural electrode fingers of the other comb-shaped electrode. Electrode 707 is made of the same material as electrodes 703 and 704 according to Embodiment 4, and has the same effects. Acoustic wave sensor 754 may include reflectors 713A and 713B provided on upper surface 702A of piezoelectric substrate 702. Reflectors 713A and 713B are arranged to sandwich electrode 707 between reflectors 713A and 713B in propagation direction D701 of the acoustic wave. Acoustic wave sensor 754 further includes dielectric film 706 provided on upper surface 702A of piezoelectric substrate 702 and reaction section 705 formed on upper surface 706A of dielectric film 706. Dielectric film 706 covers electrode 707 and reflectors 713A and 713B. Reaction section 705 is configures to react with or to be bound to an object, or a binding substance binding with the object. Detector 701A is configured to detect a characteristic of the main acoustic wave received by electrode 707. Groove 708 or ridge 709 is provided on upper surface 706A of dielectric film 706. Adhesive layer 711 forming reaction section 705 is formed on upper surface 706A of dielectric film 706. This configuration provide corrugate portion 711P having a groove or a ridge provided on upper surface 711A of adhesive layer 711 forming reaction section 705. Reaction section 705 is located above electrode 707.

When substance (such as breath or sample liquid) possibly containing an object is injected on reaction section 705, the mass of reaction section 705 is changed due to the attaching of the object, and hence, the characteristic of the main acoustic wave is changed. Detector 701A detects this change, thereby detecting the presence of the object or a concentration of the object.

In acoustic wave sensor 754, adhesive layer 711 forming reaction section 705 is provided on groove 708 or ridge 709 on upper surface 706A of dielectric film 706, and has a large surface area of upper surface 711A of adhesive layer 711. This configuration increases the amount of the object or the amount of the binding substance, adsorbed on reaction section 705, accordingly enhancing the detecting precision of acoustic wave sensor 754.

Figure 12:
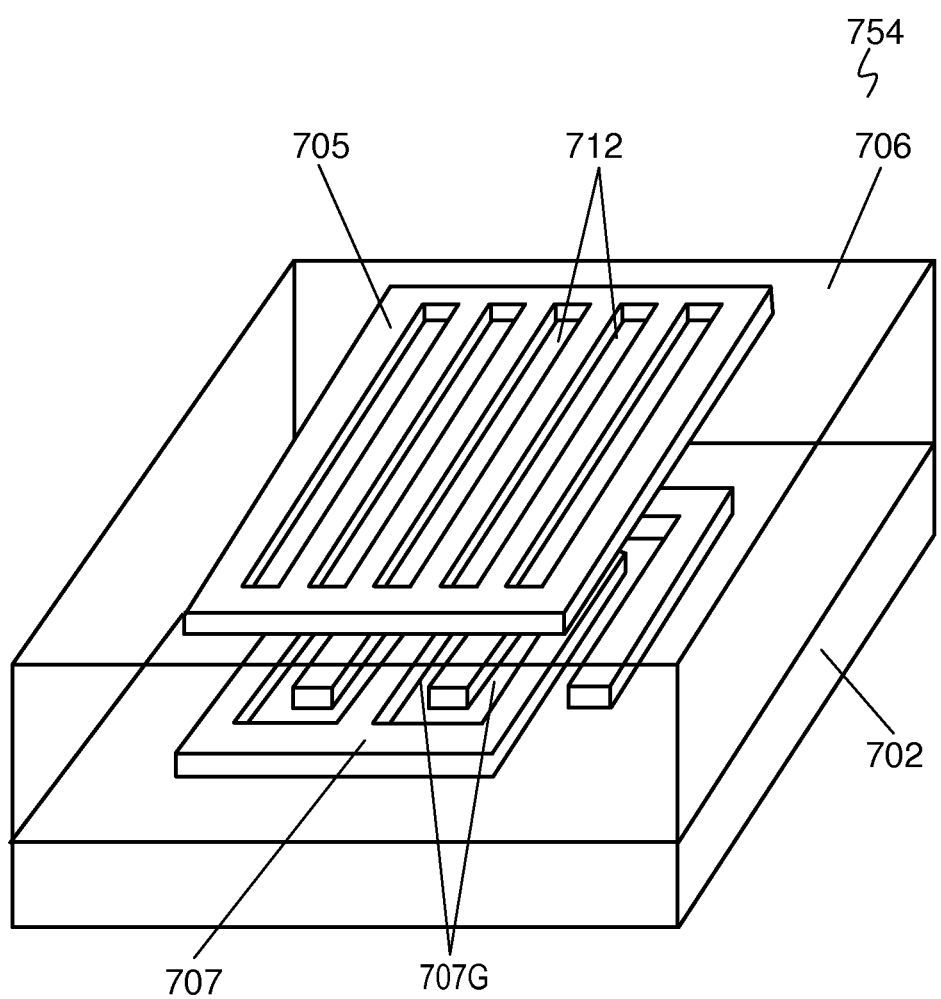
FIG. 12 is a schematic perspective view of the acoustic wave sensor according to Embodiment 5.

FIG. 12 is a schematic perspective view of acoustic wave sensor 754. As shown in FIG. 12, groove 708 is implemented by slit 712. In this case, slit 712 preferably extends perpendicularly to propagation direction D701 of the main acoustic wave, thereby reducing the propagation loss of the main acoustic wave. The width of slit 712 in propagation direction D701 may be larger than the maximum width of antibody 710 on reaction section 705, thereby allowing antibody 710 to be fixed in slit 712. Slit 712 is located above gap 707G between the electrode fingers of electrode 707 by utilizing a step between gap 707G and an upper surface of electrode 707.

As shown in FIG. 12, plural slits 712 parallel to each other are arranged in propagation direction D701 with a predetermined pitch. This pitch is different from value n·λ/2 defined by integer n and wavelength λ of the acoustic wave. This configuration prevents noise superposition caused by the reflection of unnecessary wave on plural slits 712. The pitch of slits 712 in propagation direction D701 of the main acoustic wave is preferably determined to be λ/4+n·λ/2. This configuration suppresses the noise superposition caused by the reflection of unnecessary wave on plural slits 712.

Figure 13:
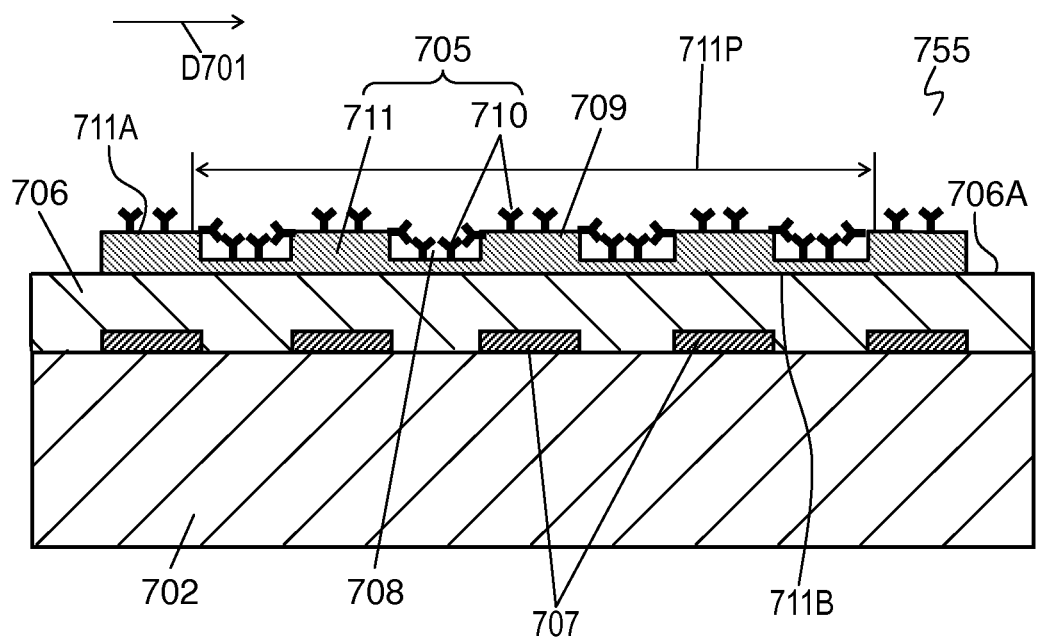
FIG. 13 is a schematic cross-sectional view of another acoustic wave sensor according to Embodiment 5.

FIG. 13 is a schematic cross-sectional view of another acoustic wave sensor 755 according to Embodiment 5. In FIG. 13, components identical to those of acoustic wave sensor 754 shown in FIGS. 10 to 12 are denoted by the same reference numerals. In acoustic wave sensor 755 shown in FIG. 13, upper surface 706A of dielectric film 706 and lower surface 711B of adhesive layer 711 are flat, and groove 708 or ridge 709 is formed on upper surface 711A of adhesive layer 711 on reaction section 705. Groove 708 or ridge 709 on upper surface 711A of adhesive layer 711 is formed by a process for fabricating adhesive layer 711 on upper surface 706A of dielectric film 706 by sputtering or vapor deposition, and then, adhesive layer 711 is etched into a predetermined shape by dry etching.

The groove or ridge formed on upper surface 711A of adhesive layer 711 of reaction section 705 increases the surface area of upper surface 711A of adhesive layer 711, and accordingly, increases the amount of the object or the amount of the binding substance, adsorbed on reaction section 705, thereby enhancing the detecting precision of acoustic wave sensor 755.

Exemplary Embodiment 6

Figure 14B:
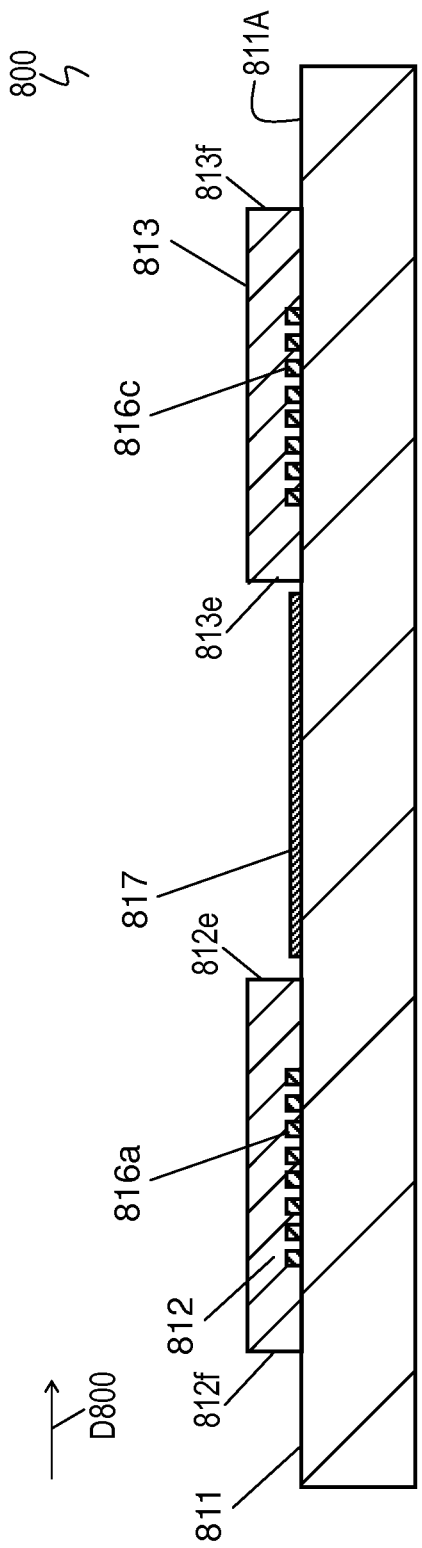
FIG. 14B is a schematic cross-sectional view of the acoustic wave sensor on line 14B-14B shown in FIG. 14A.

FIG. 14A is a schematic top view of acoustic wave sensor 800 according to Exemplary Embodiment 6. FIG. 14B is a schematic cross-sectional view of acoustic wave sensor 800 on line 14B-14B shown in FIG. 14A. Acoustic wave sensor 800 is a biosensor employing a transversal type acoustic wave element, and detects an object, such as protein, gene, or signal molecule, based upon a molecule recognition mechanism of a biological body.

Acoustic wave sensor 800 includes piezoelectric substrate 811, transmitting electrode portion 814 configured to transmit an acoustic wave propagating through upper surface 811A of piezoelectric substrate 811, receiving electrode portion 815 configured to receive the acoustic wave propagating through upper surface 811A of piezoelectric substrate 811, reaction section 817 provided at a propagation path between transmitting electrode portion 814 and receiving electrode portion 815, transmitting electrode cover 812 that covers and protects transmitting electrode portion 814, and receiving electrode cover 813 that covers and protects receiving electrode portion 815. Liquid as a sample is injected into reaction section 817. Detector 800A detects a characteristic (phase, or frequency) of the main acoustic wave received by receiving electrode portion 815. In acoustic wave sensor 800 according to Embodiment 6, detector 800A detects the frequency change or the phase change of the main acoustic wave received by receiving electrode portion 815. Detector 800A may detect the change in the other characteristics, such as a velocity, amplitude, or wavelength, of the main acoustic wave. The acoustic wave may be a surface acoustic wave, such as Shear-Horizontal wave or a Rayleigh wave, or a bulk wave, such as a plate wave. The acoustic wave propagates from transmitting electrode portion 814 to receiving electrode portion 815 in propagation direction D800. Transmitting electrode cover 812 entirely covers transmitting electrode portion 814 in at least propagation direction D800 and a direction opposite to the propagation direction. Receiving electrode cover 813 entirely covers receiving electrode portion 815 in at least propagation direction D800 and a direction opposite to the propagation direction.

Piezoelectric substrate 811 is a single crystal substrate made of a piezoelectric material such as quartz, lithium tantalate ($LiTaO_3$), or lithium niobate ($LiNbO_3$), or lithium tetraborate ($Li_2B_4O_7$). Transmitting electrode portion 814 and receiving electrode portion 815 are made of a metal material, such as aluminum (Al), gold (Au), copper (Cu), titanium (Ti), or molybdenum (Mo).

Transmitting electrode cover 812 and receiving electrode cover 813 may be made of a dielectric film, such as silicon dioxide ($SiO_2$), or may be a cap made of metal, such as iron (Fe), that seals transmitting electrode portion 814 and receiving electrode portion 815 air-tightly with a vibration space formed on transmitting electrode portion 814 and receiving electrode portion 815. In the case that transmitting electrode cover 812 and receiving electrode cover 813 are made of dielectric films, the thickness and material of the dielectric films are determined to allow the wave propagating through each electrode portion to become a boundary acoustic wave propagating on the boundary between piezoelectric substrate 811 and each of the dielectric films.

An adhesive layer made of a metal, such as gold, is formed on reaction section 817, and an antibody is further formed on the adhesive layer. When a sample (such as breath or solution) possibly containing the object is injected into the antibody, the object is collected by the antibody due to an antigen-antibody reaction or adsorption. In this case, the propagation characteristic of the acoustic wave propagating through piezoelectric substrate 811 changes due to the change in a mass of the antibody before and after the injection of the sample. Detector 800A detects the change in the propagation characteristic of the acoustic wave before and after the injection of the sample, thereby detecting the presence of the object or the concentration of the object in the sample.

The adhesive layer on reaction section 817 may be made of resin, such as paraxylylene-based polymer, instead of metal.

Transmitting electrode portion 814 includes transmitting electrodes 814*a* and 814*b* having different propagation paths of the acoustic wave. Transmitting electrode 814*a* includes bus bar 818, plural electrode fingers 816*a* extending perpendicularly to propagation direction D800 from bus bar 818, bus bar 819, and plural electrode fingers 816*a* extending perpendicularly to propagation direction D800 from bus bar 819. Plural electrode fingers 816*a* extending from bus bar 818 are arranged to interdigitate with plural electrode fingers 816*a* extending from bus bar 819, so that transmitting electrode 814*a* forms an interdigital transducer (IDT) electrode. Transmitting electrode 814*b* includes bus bar 819, plural electrode fingers 816*b* extending perpendicular to propagation direction D800 from bus bar 819, bus bar 820, and plural electrode fingers 816*b* extending perpendicularly to propagation direction D800 from bus bar 820. Plural electrode fingers 816*b* extending from bus bar 819 are arranged to interdigitate with plural electrode fingers 816*b* extending from bus bar 820, so that transmitting electrode 814*b* forms an interdigital transducer (IDT) electrode. Two IDT electrodes, i.e., transmitting electrodes 814*a* and 814*b* of transmitting electrode portion 814 are connected in cascade connection with each other by sharing bus bar 819. Receiving electrode portion 815 includes receiving electrodes 815*a* and 815*b* having different propagation paths of the acoustic wave. Receiving electrode 815*a* includes bus bar 821, plural electrode fingers 816*c* extending perpendicularly to propagation direction D800 from bus bar 821, bus bar 822, and plural electrode fingers 816*c* extending perpendicularly to propagation direction D800 from bus bar 822. Plural electrode fingers 816*c* extending from bus bar 821 are arranged to interdigitate with plural electrode fingers 816*c* extending from bus bar 822, so that receiving electrode 815*a* forms an interdigital transducer (IDT) electrode. Receiving electrode 815*b* includes bus bar 822, plural electrode fingers 816*d* extending perpendicularly to propagation direction D800 from bus bar 822, bus bar 823, and plural electrode fingers 816*d* extending perpendicularly to propagation direction D800 from bus bar 823. Plural electrode fingers 816*d* extending from bus bar 822 are arranged to interdigitate with plural electrode fingers 816*d* extending from bus bar 823, so that receiving electrode 815*b* forms an interdigital transducer (IDT) electrode. Two IDT electrodes, i.e., receiving electrodes 815*a* and 815*b* of receiving electrode portion 815 are connected in cascade connection with each other by sharing bus bar 819. According to Embodiment 6, the width of each of electrode fingers 816*a* to 816*d* in propagation direction D800 is $\lambda/8$.

Transmitting electrode 814*a* and receiving electrode 815*a* are provided on the propagation path through which the acoustic wave propagates, and form propagation region 811P on upper surface 811A of piezoelectric substrate 811 between line B1 and line B2. The acoustic wave has a wavelength $\lambda$ determined by the pitch of electrode fingers 816*a*. Transmitting electrode 814*b* and receiving electrode 815*b* are formed on a propagation path through which the acoustic wave propagates, and form propagation region 811Q on upper surface 811A of piezoelectric substrate 811 between line B3 and line B4. The acoustic wave has wavelength $\lambda$ determined by the pitch of electrode fingers 816*b*. Transmitting electrode cover 812 has end 812*e* facing reaction section 817. Transmitting electrode cover 812 is arranged such that the difference between distance d11 between transmitting electrode 814*a* and transmitting electrode cover 812 and distance d12 between transmitting electrode 814*b* and end 812*e* of transmitting electrode cover 812 becomes $\lambda/4+n\cdot\lambda/2$ in propagation direction D800 (n is an integer). Distance d11 is a distance between end 812*e* and electrode finger 816*a* which is the closest to reaction section 817 among plural electrode fingers 816*a* of transmitting electrode 814*a* in propagation direction D800. Distance d12 is a distance between end 812*e* and electrode finger 816*b* which is the closest to reaction section 817 among plural electrode fingers 816*b* of transmitting electrode 814*b* in propagation direction D800. Receiving electrode cover 813 has end 813*e* opposite to reaction section 817. Receiving electrode cover 813 is arranged such that the difference between distance d13 between receiving electrode 815*a* and end 813*e* of receiving electrode cover 813 and distance d14 between receiving electrode 815*b* and end 813*e* of receiving electrode cover 813 becomes $\lambda/4+m\cdot\lambda/2$ in propagation direction D800 (m is an integer). Distance d13 is a distance between end 813*e* and electrode finger 816*c* which is the closest to reaction section 817 among plural electrode fingers 816*c* of receiving electrode 815*a* in propagation direction D800. Distance d14 is a distance between end 813*e* and electrode finger 816*d* which is the closest to reaction section 817 among plural electrode fingers 816*d* of receiving electrode 815*b* in propagation direction D800.

When the transmitting electrode portion and the receiving electrode portion of the acoustic wave sensor are covered by the covers, a difference in acoustic impedance is generated on the boundary between the reaction section that is not covered by the cover and each of the transmitting electrode portion and the receiving electrode portion that are covered by the covers. This difference may cause reflection of the acoustic wave.

Figure 22A:
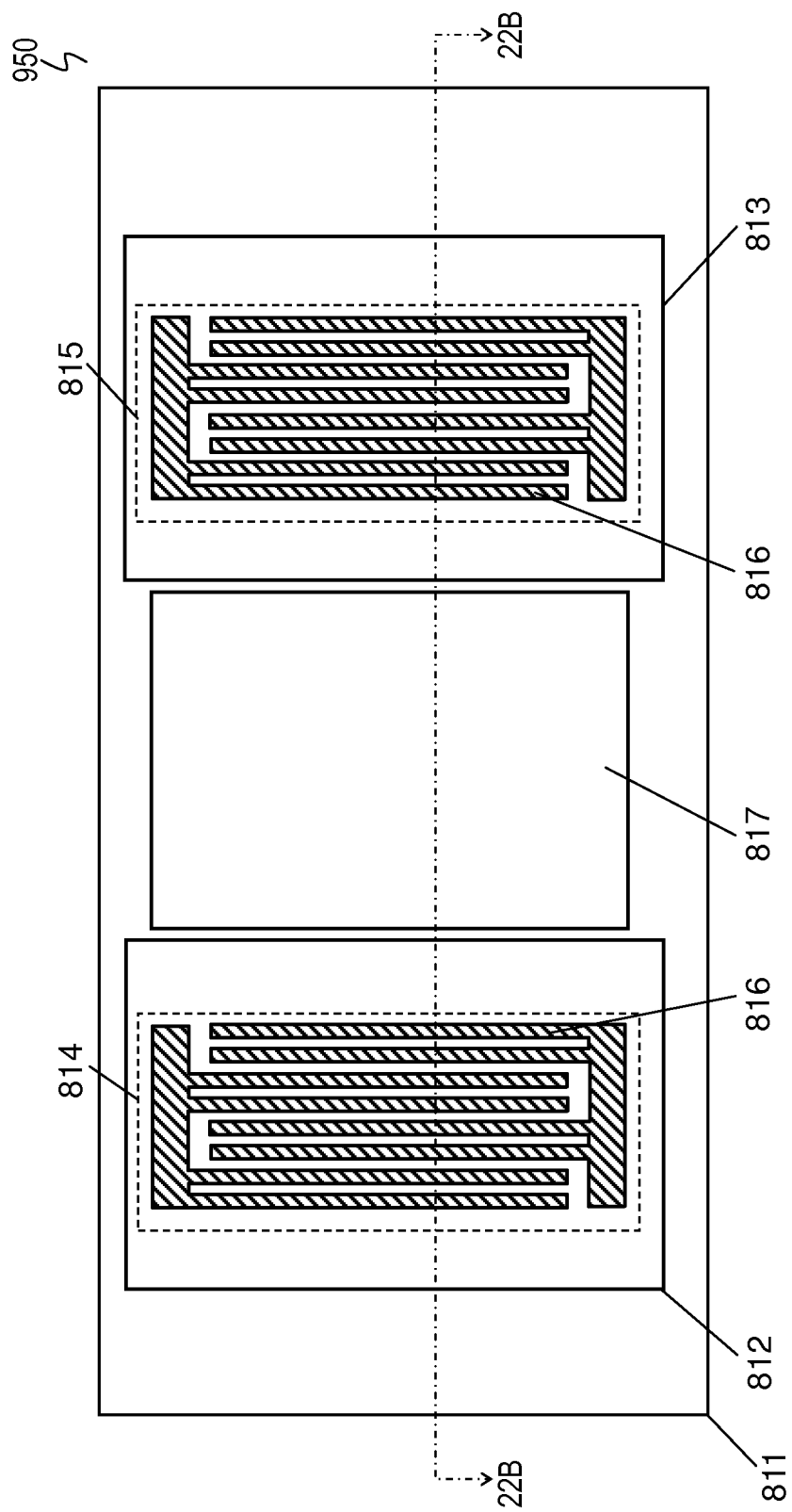
FIG. 22A is a schematic top view of still another acoustic wave sensor.
Figure 22B:
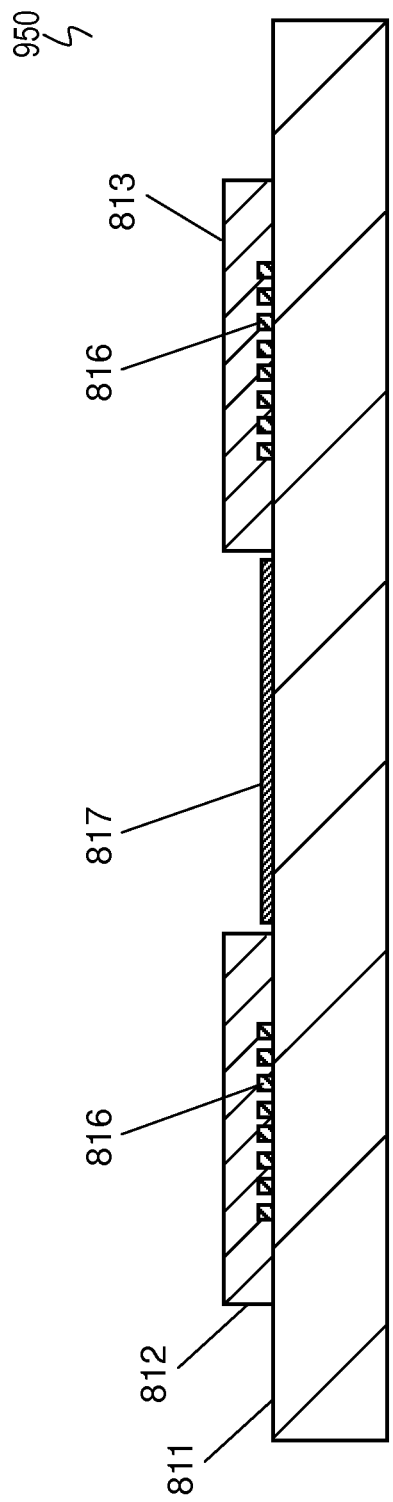
FIG. 22B is a schematic cross-sectional view of the acoustic wave sensor on line 22B-22B shown in FIG. 22A.

In conventional acoustic wave sensor 950 shown in FIGS. 22A and 22B, the acoustic wave excited by transmitting electrode portion 814 propagates toward receiving electrode portion 815 as a traveling wave. A part of the excited acoustic wave is reflected on the end of transmitting electrode cover 812 to cause a reflection wave. The reflection wave is again excited by transmitting electrode portion 814, and propagates toward receiving electrode portion 815. The phase of the acoustic wave again excited may not coincide with the phase of the traveling wave, which is a main response. Acoustic wave sensor 950 has an operation principle and electric characteristic similar to those of a transversal type filter. Therefore, when the above-mentioned reflection is generated, this reflection wave generates a pass-band ripple or a group delay ripple. The pass-band ripple or the group delay ripple on the frequency range used for the detection may cause sensitivity degradation or malfunction of acoustic wave sensor 950.

In acoustic wave sensor 800 according to Embodiment 6, the acoustic wave excited by transmitting electrode 814*a* and reflected on end 812*e* of transmitting electrode cover 812 is again excited by transmitting electrode 814*a*, and propagates toward receiving electrode portion 815. The acoustic wave excited by transmitting electrode 814*b* and reflected on end 812*e* of transmitting electrode cover 812 is again excited by transmitting electrode 814*b*, and propagates toward receiving electrode portion 815. Distances d11 and d12 determined as described above causes the phase of the acoustic wave excited again by transmitting electrode 814*a* and propagates toward receiving electrode portion 815 to become opposite to the phase of the acoustic wave excited again by transmitting electrode 814*b* and propagates toward receiving electrode portion 815. Accordingly, these acoustic waves are canceled, and prevent the characteristic of the acoustic wave from being influenced by the reflection on end 812*e* of cover 812.

In acoustic wave sensor 800 according to Embodiment 6, a part of the acoustic wave propagating from transmitting electrode 814*a* is reflected by receiving electrode 815*a*, is reflected again by end 813*e* of receiving electrode cover 813, and reaches receiving electrode 815*a*. A part of the acoustic wave excited by transmitting electrode 814*b* and propagating is reflected on receiving electrode 815*b*, is reflected again on end 813*e* of receiving electrode cover 813, and reaches receiving electrode 815*b*. Distances d13 and d14 determined as described above causes the phase of the acoustic wave reflected again by end 813*e* of receiving electrode cover 813 and reaching receiving electrode 815*a* to become opposite to the phase of the acoustic wave reflected again by end 813*e* of receiving electrode cover 813 and reaching receiving electrode 815*b*. Accordingly, these acoustic waves are canceled, and prevent the characteristic of the acoustic wave from influenced by the reflection on end 813*e* of cover 813. As described above, acoustic wave sensor 800 prevents a ripple produced on the characteristic, hence having excellent sensor sensitivity and fewer malfunctions.

Acoustic wave sensor 800 according to Embodiment 6 satisfies at least one of a condition that the difference between distance d11 and distance d12 is $\lambda/4+n\cdot\lambda/2$ and a condition that the difference between distance d13 and distance d14 is $\lambda/4+m\cdot\lambda/2$, thereby providing the above effects.

Transmitting electrode cover 812 has end 812*f* opposite to end 812*e* in propagation direction D800. Since the acoustic wave excited by transmitting electrodes 814*a* and 814*b* propagates bi-directionally, the difference between distance d21 from transmitting electrode 814*a* to end 812*f* of transmitting electrode cover 812 and distance d22 from transmitting electrode 814*b* to end 812*f* of transmitting electrode cover 812 in propagation direction D800 is preferably $\lambda/4+p\cdot\lambda/2$ (p is an integer). Distance d21 is a distance between end 812*f* and electrode finger 816*a* which is the closest to end 812*f* of transmitting electrode cover 812 among plural electrode fingers 816*a* of transmitting electrode 814*a* in propagation direction D800. Distance d22 is a distance between end 812*f* and electrode finger 816*b* which is the closest to end 812*f* of transmitting electrode cover 812 among plural electrode fingers 816*b* of transmitting electrode 814*b* in propagation direction D800. Similarly, receiving electrode cover 813 has end 813*f* opposite to end 813*e* in propagation direction D800. The acoustic wave excited by receiving electrodes 815*a* and 815*b* propagates bi-directionally. Therefore, the difference between distance d23 from receiving electrode 815*a* to end 813*f* of receiving electrode cover 813 and distance d24 from receiving electrode 815*b* to end 813*f* of receiving electrode cover 813 in propagation direction D800 is preferably $\lambda/4+q\cdot\lambda/2$ (q is an integer). Distance d23 is a distance between end 813*f* and electrode finger 816*c* which is the closest to end 813*f* of receiving electrode cover 813 among plural electrode fingers 816*c* of receiving electrode 815*a* in propagation direction D800. Distance d24 is a distance between end 813*f* and electrode finger 816*d* which is the closest to end 813*f* of receiving electrode cover 813 among plural electrode fingers 816*d* of receiving electrode 815*b* in propagation direction D800.

Distance L1 between the center of transmitting electrode 814*a* in propagation direction D800 and the center of receiving electrode 815*a* in propagation direction D800 is preferably substantially equal to distance L2 between the center of transmitting electrode 814*b* in propagation direction D800 and the center of receiving electrode 815*b* in propagation direction D800 in order to allow the delay time of the acoustic wave on propagation region 811P to be identical to the delay time of the acoustic wave on propagation region 811Q. This configuration can enhance sensitivity of a biomolecular measurement device or a detection device employing acoustic wave sensor 800 in a sensor circuit as a delay line.

Each of transmitting electrode 814*a*, transmitting electrode 814*b*, receiving electrode 815*a*, and receiving electrode 815*b* shown in FIG. 14A is a so-called split finger electrode including a pair of comb-shaped electrodes, but it is not particularly limited thereto. Each of transmitting electrode 814*a*, transmitting electrode 814*b*, receiving electrode 815*a*, and receiving electrode 815*b* may be a solid electrode or a unidirectional electrode.

The similar effect can be obtained even if distances d11 to d14 do not completely satisfy the relation described above. In acoustic wave sensor 800 according to Embodiment 6, the difference between distances d11 and d12 is different from $n\cdot\lambda/2$. This configuration allows the phase of the acoustic wave excited again by transmitting electrode 814*a* and propagates toward receiving electrode portion 815 to be close to the phase reverse to the phase of the acoustic wave excited again by transmitting electrode 814*b* and propagates toward receiving electrode portion 815. Accordingly, these acoustic waves are canceled and become too weak, accordingly preventing the characteristic of the acoustic wave from being influenced by the reflection on end 812*e*.

In acoustic wave sensor 800 according to Embodiment 6, the difference between distances d13 and d14 is different from $m\cdot\lambda/2$. This configuration allows the phase of the acoustic wave reflected again by end 813*e* of receiving electrode cover 813 and reaching receiving electrode 815*a* to be close to the phase opposite to the phase of the acoustic wave reflected again by end 813*e* of receiving electrode cover 813 and reaching receiving electrode 815*b*. Accordingly, these acoustic waves are canceled and become too weak, accordingly preventing the characteristic of the acoustic wave from being influenced by the reflection on end 813*e* of the cover 813. Consequently, acoustic wave sensor 800 prevents ripple on the characteristic from occurring, hence having excellent sensor sensitivity and less malfunction.

Acoustic wave sensor 800 according to Embodiment 6 satisfies at least one of a condition that the difference between distance d11 and distance d12 is different from $n\cdot\lambda/2$ and a condition that the difference between distance d13 and distance d14 is different from $m\cdot\lambda/2$, providing the above effects.

Exemplary Embodiment 7

Figure 15:
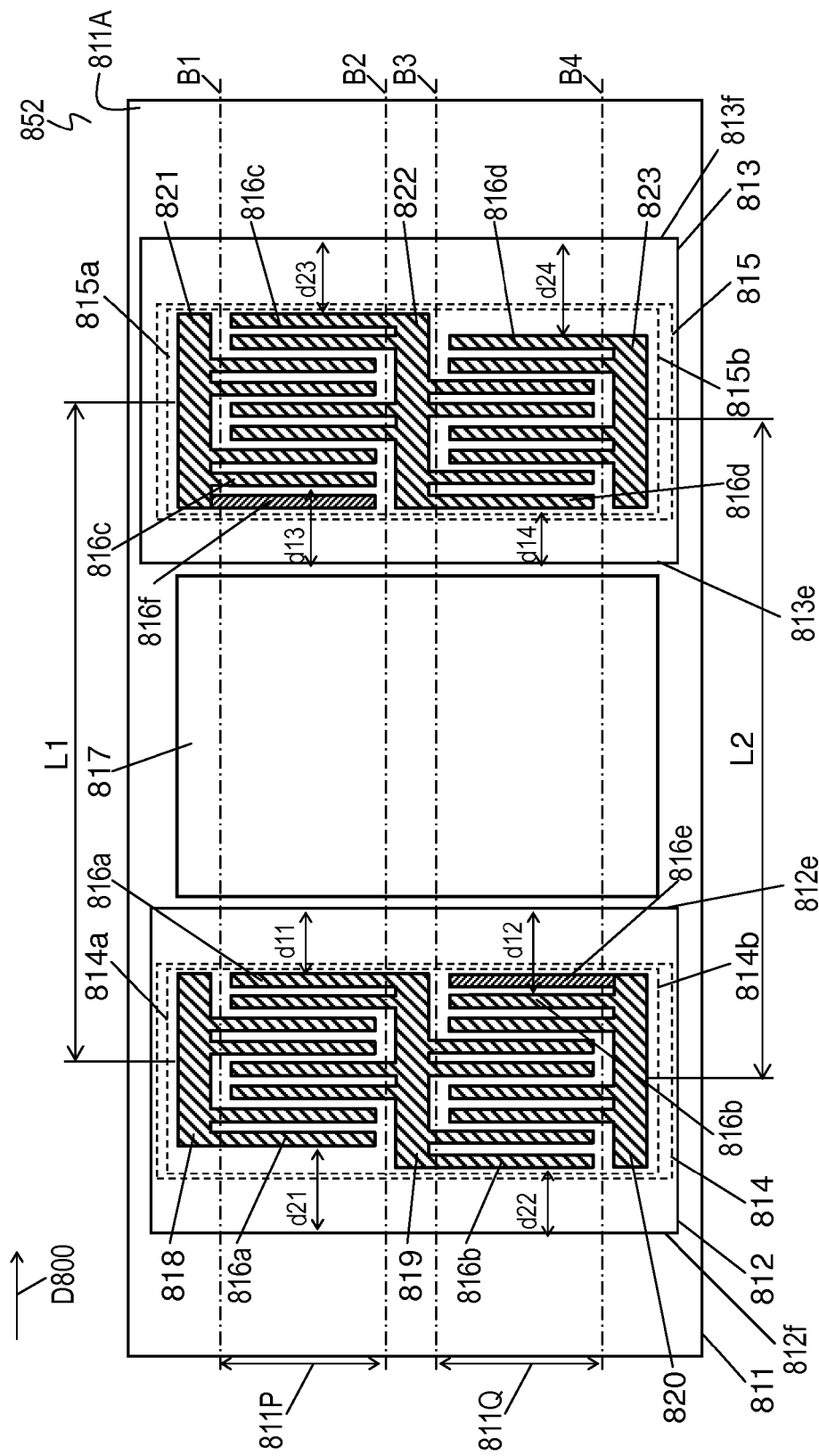
FIG. 15 is a schematic top view of an acoustic wave sensor according to Exemplary Embodiment 7.

FIG. 15 is a schematic top view of acoustic wave sensor 852 according to exemplary Embodiment 7. In FIG. 15, components identical to those of acoustic wave sensor 800 shown in FIGS. 14A and 14B are denoted by the same reference numerals. In acoustic wave sensor 852 according to Embodiment 7, transmitting electrode 814*b* of transmitting electrode portion 814 further includes dummy electrode finger 816*e* extending from bus bar 820 perpendicularly to propagation direction D800. Electrode fingers 816*b* and 816*e* are arranged in propagation direction D800 such that dummy electrode finger 816*e* is the closest to reaction section 817 among electrode fingers 816*b* and 816*e*. Dummy electrode finger 816*e* does not contribute to the excitation of the acoustic wave. Specifically, dummy electrode finger 816*e* is connected to the same bus bar 820 as adjacent electrode finger 816*b* and still adjacent electrode finger 816*b*, and thus three electrode fingers are consecutively connected to the same bus bar 820. Therefore, dummy electrode finger 816*e* does not substantially contribute to the excitation of the acoustic wave. Accordingly, in acoustic wave sensor 852 shown in FIG. 15, distance d12 is the distance between end 812e of transmitting electrode cover 812 and electrode finger 816b which is the closest to reaction section 817 among plural electrode fingers 816b of transmitting electrode 814b. Acoustic wave sensor 852 has a function of adjusting a velocity from transmitting electrode 814b to end 812e of transmitting electrode cover 812. Dummy electrode finger 816e can adjust the velocity in order that the phase of the acoustic wave excited again by transmitting electrode 814a and propagating to receiving electrode portion 815 becomes completely opposite to the phase of the acoustic wave excited again by transmitting electrode 814b and propagating to receiving electrode portion 815. Accordingly, these acoustic waves are canceled, and prevent the characteristic of the acoustic wave from being influenced by the reflection on end 812e of cover 812.

In acoustic wave sensor 852 according to Embodiment 7, receiving electrode 815b of receiving electrode portion 815 further includes dummy electrode finger 816f extending from bus bar 821 perpendicularly to propagation direction D800. Electrode fingers 816c and 816f are arranged in propagation direction D800 such that dummy electrode finger 816f is the closest to reaction section 817 among electrode fingers 816c and 816f. Dummy electrode finger 816f does not substantially contribute to the excitation of the acoustic wave. Specifically, dummy electrode finger 816f is connected to the same bus bar 821 as adjacent electrode finger 816c and still adjacent electrode finger 816c, and thus, three electrode fingers are consecutively connected to the same bus bar 821. Therefore, dummy electrode finger 816f does not substantially contribute to the excitation of the acoustic wave. Accordingly, in acoustic wave sensor 852 shown in FIG. 15, distance d13 is the distance between end 813e of receiving electrode cover 813 and electrode finger 816c which is the closest to reaction section 817 among plural electrode fingers 816c of receiving electrode 815b. Acoustic wave sensor 852 has a function of adjusting a velocity from receiving electrode 815b to end 813e of receiving electrode cover 813. Dummy electrode finger 816f can adjust the velocity in order that the phase of the acoustic wave reflected again by end 813e of receiving electrode cover 813 and reaching receiving electrode 815a becomes opposite to the phase of the acoustic wave reflected again on end 813e of receiving electrode cover 813 and reaching receiving electrode 815b. Accordingly, these acoustic waves are canceled, and prevent the characteristic of the acoustic wave from being influenced by the reflection on end 813e of cover 813.

As described above, in acoustic wave sensor 852 according to Embodiment 7, distance d11 is the distance between end 812e of transmitting electrode cover 812 and electrode finger 816a which is the closest to reaction section 817 among plural electrode fingers 816a of transmitting electrode 814a substantially contributing to the excitation of the acoustic wave in propagation direction D800. Distance d12 is the distance between end 812e of transmitting electrode cover 812 and electrode finger 816b which is the closest to reaction section 817 among plural electrode fingers 816b of transmitting electrode 814b substantially contributing to the excitation of the acoustic wave in propagation direction D800. Distance d13 is the distance between end 813e of receiving electrode cover 813 and electrode finger 816c which is the closest to reaction section 817 among plural electrode fingers 816c of receiving electrode 815a substantially contributing to the receiving of the acoustic wave in propagation direction D800. Distance d14 is the distance between end 813e of receiving electrode cover 813 and electrode finger 816d which is the closest to reaction section 817 among plural electrode fingers 816d of receiving electrode 815b substantially contributing to the receiving of the acoustic wave in propagation direction D800.

Exemplary Embodiment 8

Figure 16:
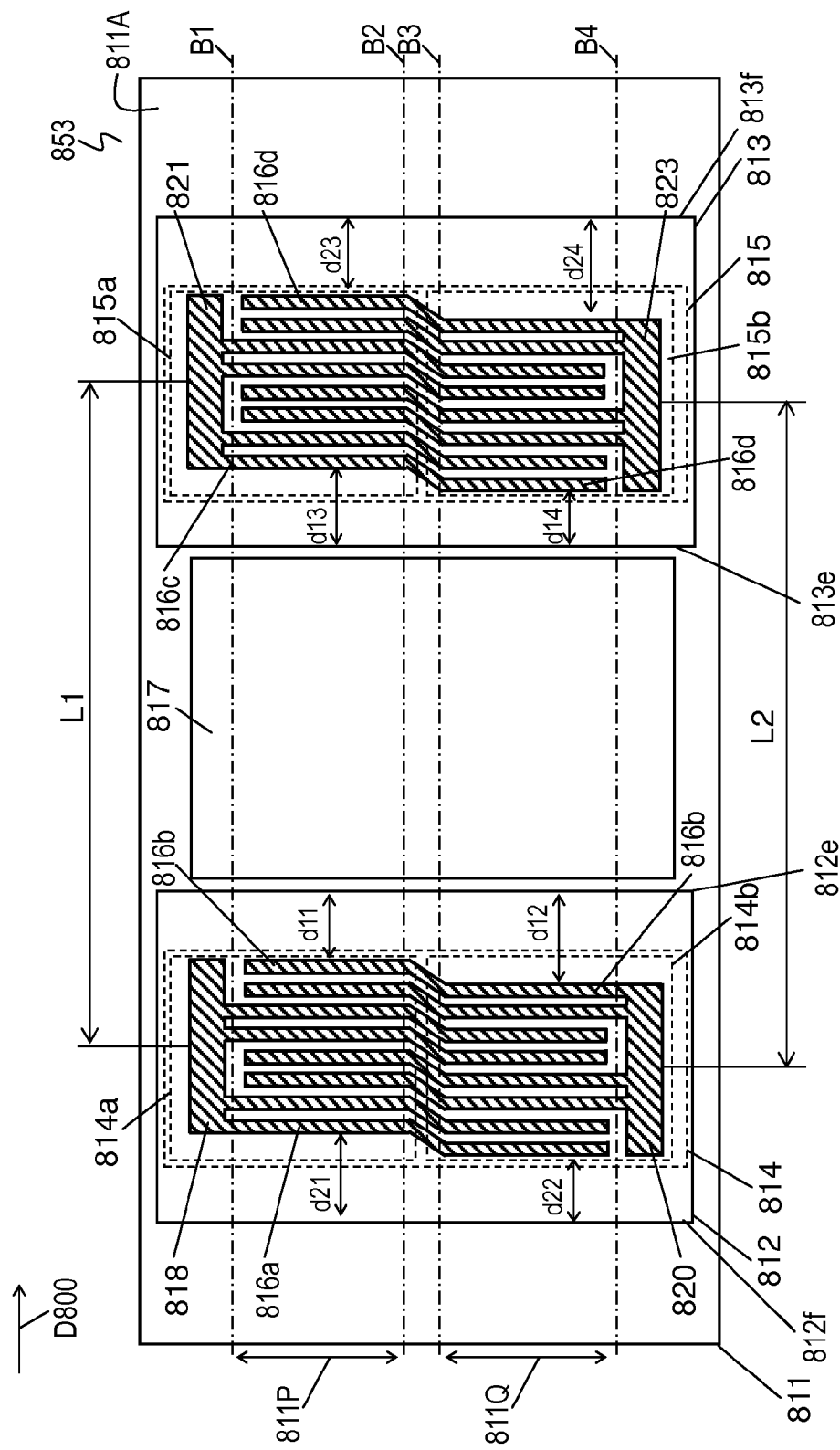
FIG. 16 is a schematic top view of an acoustic wave sensor according to Exemplary Embodiment 8.

FIG. 16 is a schematic top view of acoustic wave sensor 853 according to Exemplary Embodiment 8. In FIG. 16, components identical to those of acoustic wave sensor 800 according to Embodiment 6 shown in FIGS. 14A and 14B are denoted by the same reference numerals. In acoustic wave sensor 853 according to Embodiment 8, transmitting electrode portion 814 does not include bus bar 819 shown in FIG. 14A. In transmitting electrode portion 814, electrode fingers 816a extends from bus bar 818 to propagation region 811Q, while electrode fingers 816b extends form bus bar 820 to propagation region 811P. Transmitting electrode portion 814 includes a single IDT electrode including a pair of comb-shaped electrodes. Specifically, transmitting electrode 814a includes electrode fingers 816a and 816b arranged to interdigitate with each other on propagation region 811P, while transmitting electrode 814b includes electrode fingers 816a and 816b arranged to interdigitate with each other on propagation region 811Q. In acoustic wave sensor 853, receiving electrode portion 815 does not include bus bar 822 shown in FIG. 14A. In receiving electrode portion 815, electrode fingers 816c extends from bus bar 821 to propagation region 811Q while electrode fingers 816d extends form bus bar 823 to propagation region 811P. Receiving electrode portion 815 includes a single IDT electrode including a pair of comb-shaped electrodes. Specifically, receiving electrode 815a includes electrode fingers 816c and 816d arranged to interdigitate with each other on propagation region 811P, while receiving electrode 815b includes electrode fingers 816c and 816d arranged to interdigitate with each other on propagation region 811Q.

Electrode fingers 816a to 816d are bent between propagation regions 811P and 811Q, i.e., between line B2 and line B3, to extend obliquely to propagation direction D800. Electrode fingers 816a to 816d extend perpendicularly to propagation direction D800 in propagation regions 811P and 811Q. Transmitting electrode 814a is located at a position shifted from transmitting electrode 814b by $\lambda/4$ in propagation direction D800 while receiving electrode 815a is located at a position shifted from receiving electrode 815b by $\lambda/4$ in propagation direction D800 ($\lambda$ is the wavelength of the acoustic wave).

In acoustic wave sensor 853, similarly to acoustic wave sensor 800 according to Embodiment 6 shown in FIG. 14A, distance d11 is the distance between transmitting electrode 814a and end 812e of transmitting electrode cover 812 in propagation direction D800, and distance d12 is the distance between transmitting electrode 814b and end 812e of transmitting electrode cover 812 in propagation direction D800. Specifically, distance d11 is the distance between end 812e of transmitting electrode cover 812 and the electrode finger which is the closest to reaction section 817 among electrode fingers 816a and 816b of transmitting electrode 814a substantially contributing to the excitation of the acoustic wave on propagation region 811P in propagation direction D800. Distance d12 is the distance between end 812e of transmitting electrode cover 812 and the electrode finger which is the closest to reaction section 817 among electrode fingers 816a and 816b of transmitting electrode 814b substantially contributing to the excitation of the acoustic wave on propagation region 811Q in propagation direction D800. Distance d11 is shorter than distance d12 by $\lambda/4$. Similarly, distance d13 is the distance between receiving electrode 815a and end 813e of receiving electrode cover 813 in propagation direction D800, and distance d14 is the distance between receiving electrode 815b and end 813e of receiving electrode cover 813 in propagation direction D800. Specifically, distance d13 is the distance between end 813e of receiving electrode cover 813 and the electrode finger which is the closest to reaction section 817 among electrode fingers 816c and 816d of receiving electrode 815a substantially contributing to the receiving of the acoustic wave on propagation region 811P in propagation direction D800. Distance d14 is the distance between end 813e of receiving electrode cover 813 and the electrode finger which is the closest to reaction section 817 among electrode fingers 816c and 816d of receiving electrode 815b substantially contributing to the receiving of the acoustic wave on propagation region 811Q in propagation direction D800. Distance d14 is shorter than distance d13 by $\lambda/4$. This configuration provides an effect similar to the effect of acoustic wave sensor 800 according to Embodiment 6. Specifically, the phase of the acoustic wave which is excited by transmitting electrode 814a, is reflected on the end of transmitting electrode cover 812, is excited again by transmitting electrode 814a, and propagates to receiving electrode portion 815 becomes opposite to the phase of the acoustic wave which is excited by transmitting electrode 814b, is reflected on the end of transmitting electrode cover 812, is excited again by transmitting electrode 814b, and propagates to receiving electrode portion 815. Accordingly, these acoustic waves are canceled, and prevent the characteristic of the acoustic wave from being influenced by the reflection on end 812e of cover 812. Similarly, the phase of a part of the acoustic wave propagating from transmitting electrode 814a, is reflected on receiving electrode 815a, is reflected again on end 813e of receiving electrode cover 813, and reaching receiving electrode 815a becomes opposite to the phase of a part of the acoustic wave propagating from transmitting electrode 814b, is reflected on receiving electrode 815b, is reflected again on end 813e of receiving electrode cover 813, and reaching receiving electrode 815b. Accordingly, the acoustic wave reflected again on end 813e is canceled, and prevent the characteristic of the acoustic wave from being influenced by the reflection on end 813e of cover 813 can be prevented. As described above, acoustic wave sensor 853 prevents the occurrence of ripple on the characteristic, hence having excellent sensor sensitivity and fewer malfunctions.

Acoustic wave excited by a transmitting electrode propagates bi-directionally. In acoustic wave sensor 853 according to Embodiment 7, similarly to acoustic wave sensor 800 according to Embodiment 6 shown in FIG. 14A, distance d21 is the distance between transmitting electrode 814a and end 812f of transmitting electrode cover 812 in propagation direction D800. Distance d22 is the distance between transmitting electrode 814b and end 812f of transmitting electrode cover 812 in propagation direction D800. Specifically, distance d21 is the distance between end 812f and the electrode finger which is the closest to end 812f of transmitting electrode cover 812 among electrode fingers 816a and 816b of transmitting electrode 814a substantially contributing to the excitation of the acoustic wave on propagation region 811P in propagation direction D800. Distance d22 is the distance between end 812f and electrode finger which is the closest to end 812f of transmitting electrode cover 812 among electrode fingers 816a and 816b of transmitting electrode 814b substantially contributing to the excitation of the acoustic wave on propagation region 811Q in propagation direction D800. Distance d22 is shorter than distance d21 by $\lambda/4$. Similarly, distance d23 is the distance between receiving electrode 815a and end 813f of receiving electrode cover 813 in propagation direction D800, and distance d24 is the distance between receiving electrode 815b and end 813f of receiving electrode cover 813 in propagation direction D800. Specifically, distance d23 is the distance between end 813f and the electrode finger which is the closest to end 813f of receiving electrode cover 813 among electrode fingers 816c and 816d of receiving electrode 815a substantially contributing to the receiving of the acoustic wave on propagation region 811P in propagation direction D800. Distance d24 is the distance between end 813f and the electrode finger which is the closest to end 813f of receiving electrode cover 813 among electrode fingers 816c and 816d of receiving electrode 815b substantially contributing to the receiving of the acoustic wave on propagation region 811Q in propagation direction D800. Distance d23 is shorter than distance d24 by $\lambda/4$. This configuration provides the effects of acoustic wave sensor 800 according to Embodiment 6.

Distance L1 between the center of transmitting electrode 814a in propagation direction D800 and the center of receiving electrode 815a in propagation direction D800 is preferably substantially equal to distance L2 between the center of transmitting electrode 814b in propagation direction D800 and the center of receiving electrode 815b in propagation direction D800 in order to allow the delay time of the acoustic wave on propagation region 811P to be equal to the delay time of the acoustic wave on propagation region 811Q. This configuration can enhance sensitivity of a biomolecular measurement device or a detection device employing acoustic wave sensor 852 in a sensor circuit as a delay line.

Exemplary Embodiment 9

Figure 17:
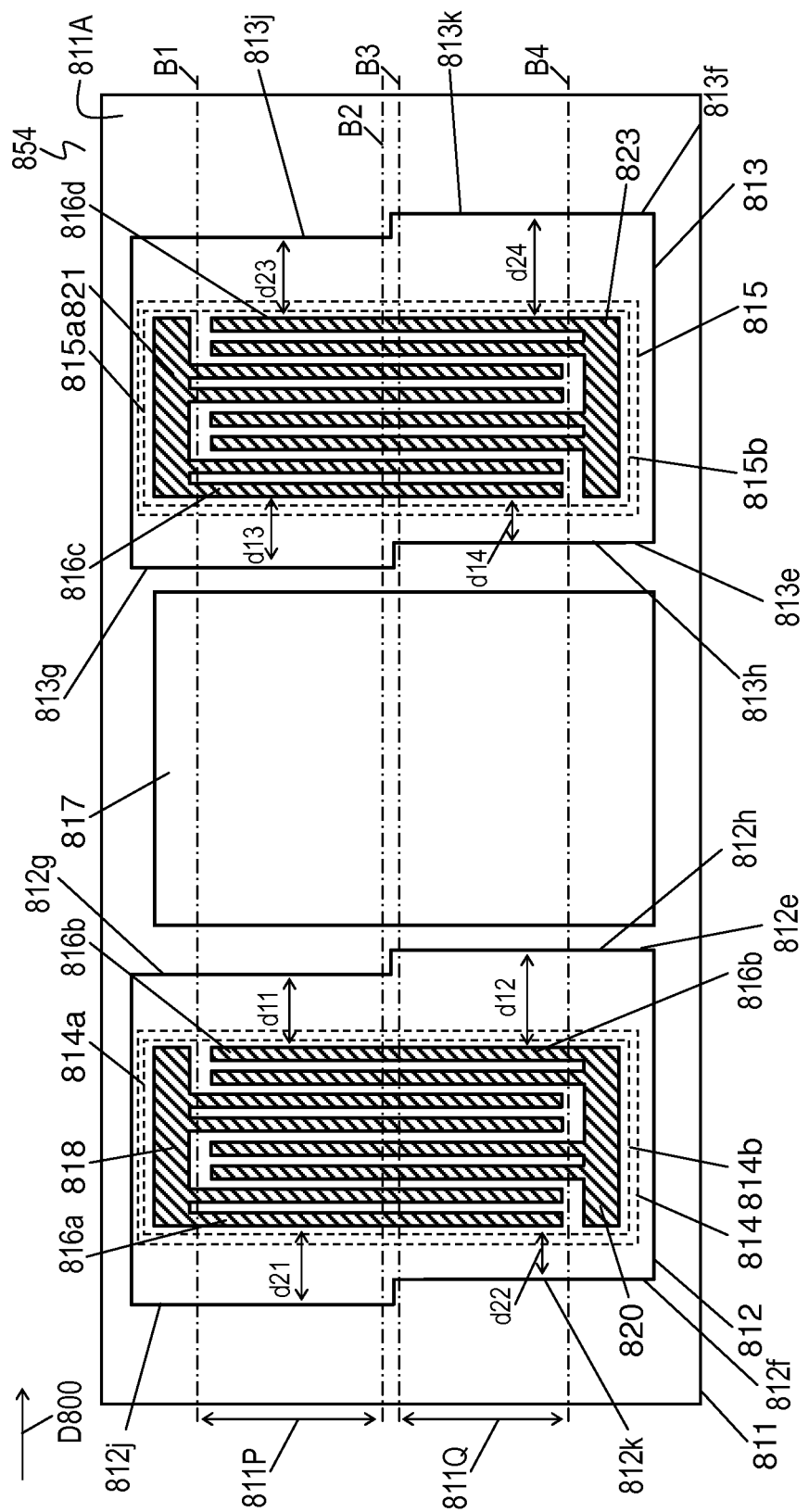
FIG. 17 is a schematic top view of an acoustic wave sensor according to Exemplary Embodiment 9.

FIG. 17 is a schematic top view of acoustic wave sensor 854 according to Exemplary Embodiment 9. In FIG. 17, components identical to those of acoustic wave sensor 853 according to Embodiment 8 shown in FIG. 16 are denoted by the same reference numerals. In acoustic wave sensor 854 according to Embodiment 9 unlike acoustic wave sensor 853 according to Embodiment 8, electrode fingers 816a and 816b of transmitting electrode portion 814 extends from bus bars 818 and 820 straight in the direction perpendicular to propagation direction D800 of the acoustic wave within the area between propagation regions 811P and 811Q, i.e., between lines B2 and B3, and interdigitate with each other. Similarly, in acoustic wave sensor 854, electrode fingers 816c and 816d of receiving electrode portion 815 extends straight in the direction perpendicular to propagation direction D800 of the acoustic wave within the area between propagation regions 811P and 811Q, i.e., between lines B2 and B3, from bus bars 821 and 823, and interdigitate with each other.

In acoustic wave sensor 854 according to Embodiment 9, not the electrode fingers but the ends of the covers are shifted between propagation regions 811P and 811Q. In acoustic wave sensor 854, end 812e of transmitting electrode cover 812 includes portion 812g located in propagation region 811P and portion 812h located in propagation region 811Q. Distance d11 is the distance between transmitting electrode 814a and portion 812g of end 812e of transmitting electrode cover 812. Distance d12 is the distance between transmitting electrode 814b and portion 812h of end 812e of transmitting electrode cover 812. Portions 812g and 812h of end 812e of transmitting electrode cover 812 are located such that the difference between distance d11 and distance d12 is $\lambda/4 + n \cdot \lambda/2$. Similarly, end 813e of receiving electrode cover 813 includes portion 813g located in propagation region 811P and portion 813h located in propagation region 811Q. Distance d13 is the distance between receiving electrode 815a and portion 813g of end 813e of receiving electrode cover 813. Distance d14 is the distance between receiving electrode 815b and portion 813h of end 813e of receiving electrode cover 813. Portions 813g and 813h of end 813e of receiving electrode cover 813 are located such that the difference between distance d13 and distance d14 is λ/4+m·λ/2.

This configuration allows the phase of the acoustic wave which is excited by transmitting electrode 814a, is reflected on portion 812g of end 812e of transmitting electrode cover 812, is excited again by transmitting electrode 814a, and propagates to receiving electrode portion 815 to become opposite to the phase of the acoustic wave which is excited by transmitting electrode 814b, is reflected on portion 812h of end 812e of transmitting electrode cover 812, is excited again by transmitting electrode 814b, and propagates to receiving electrode portion 815. Accordingly, these acoustic waves are canceled, and prevent the characteristic of the acoustic wave from being influenced by the reflection on end 812e of cover 812. Similarly, the phase of a part of the acoustic wave propagating from transmitting electrode 814a, is reflected on receiving electrode 815a, is reflected again on portion 813g of end 813e of receiving electrode cover 813, and reaching receiving electrode 815a becomes opposite to the phase of a part of the acoustic wave propagating from transmitting electrode 814b, is reflected on receiving electrode 815b, is reflected again on portion 813h of end 813e of receiving electrode cover 813, and reaching receiving electrode 815b. Accordingly, these acoustic waves are canceled, and prevent the characteristic of the acoustic wave from being influenced by the reflection on end 813e of cover 813. As described above, acoustic wave sensor 854 prevents the occurrence of ripple on the characteristic, hence having excellent sensor sensitivity and fewer malfunctions.

Transmitting electrode cover 812 has end 812f opposite to end 812e in propagation direction D800. End 812f of transmitting electrode cover 812 includes portion 812j located in propagation region 811P and portion 812k located in propagation region 811Q. The acoustic wave excited by transmitting electrode portion 814 propagates bi-directionally. Therefore, the difference between distance d21 between transmitting electrode 814a and portion 812j of end 812f of transmitting electrode cover 812 and distance d22 between transmitting electrode 814b and portion 812k of end 812f of transmitting electrode cover 812 in propagation direction D800 is preferably λ/4+p·λ/2 (p is an integer). Distance d21 is a distance between portion 812j of end 812f of transmitting electrode cover 812 and the electrode finger which is the closest to portion 812j of end 812f among plural electrode fingers 816a and 816b of transmitting electrode 814a in propagation direction D800. Distance d22 is a distance between portion 812k of end 812f of transmitting electrode cover 812 and the electrode finger which is the closest to portion 812k of end 812f among plural electrode fingers 816a and 816b of transmitting electrode 814b in propagation direction D800. Similarly, receiving electrode cover 813 has end 813f opposite to end 813e in propagation direction D800. End 813f of receiving electrode cover 813 includes portion 813j located in propagation region 811P and portion 813k located in propagation region 811Q. The acoustic wave received by receiving electrode portion 815 propagates bi-directionally. Therefore, the difference between distance d23 between receiving electrode 815a and portion 813j of end 813f of receiving electrode cover 813 and distance d24 between receiving electrode 815b and portion 813k of end 813f of receiving electrode cover 813 in propagation direction D800 is preferably λ/4+q·λ/2 (q is an integer). Distance d23 is a distance between portion 813j of end 813f of receiving electrode cover 813 and the electrode finger which is the closest to portion 813j of end 813f among plural electrode fingers 816c and 816d of receiving electrode 815a in propagation direction D800. Distance d24 is a distance between portion 813k of end 813f of receiving electrode cover 813 and the electrode finger which is the closest to portion 813k of end 813f among plural electrode fingers 816c and 816d of receiving electrode 815b in propagation direction D800.

In acoustic wave sensor 854 according to Embodiment 9, similarly to acoustic wave sensor 800 according to Embodiment 6 shown in FIG. 14A, transmitting electrodes 814a and 814b of transmitting electrode portion 814 may include two IDT electrodes that are connected in cascade connection with each other by sharing bus bar 819. Receiving electrodes 815a and 815b of receiving electrode portion 815 may include two IDT electrodes that are connected in cascade connection with each other by sharing bus bars 822. Even in this case, acoustic wave sensor 854 prevents the occurrence of ripple on the characteristic, hence having excellent sensor sensitivity and fewer malfunctions.

Exemplary Embodiment 10

Figure 18A:
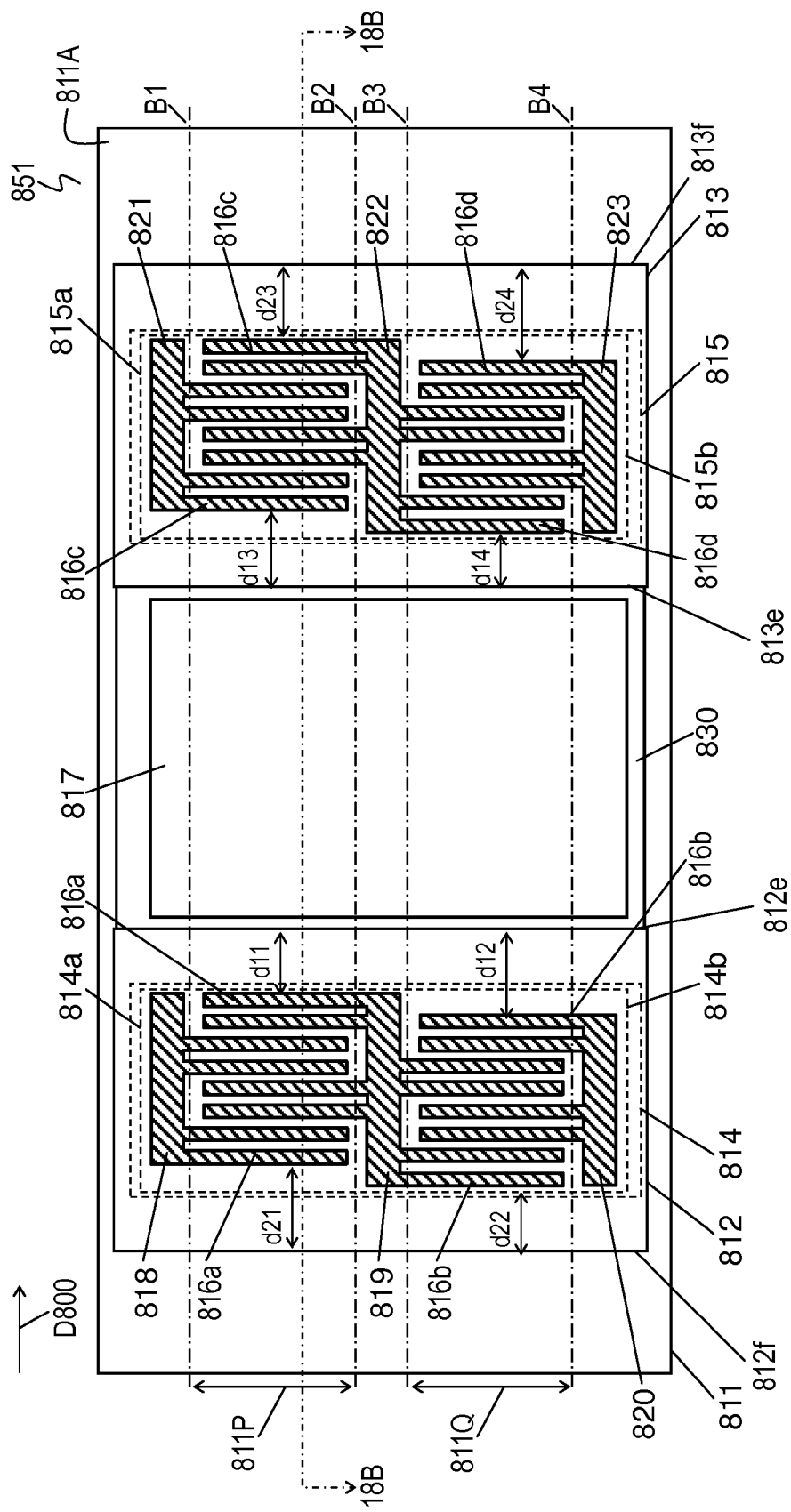
FIG. 18A is a schematic top view of an acoustic wave sensor according to Exemplary Embodiment 10.
Figure 18B:
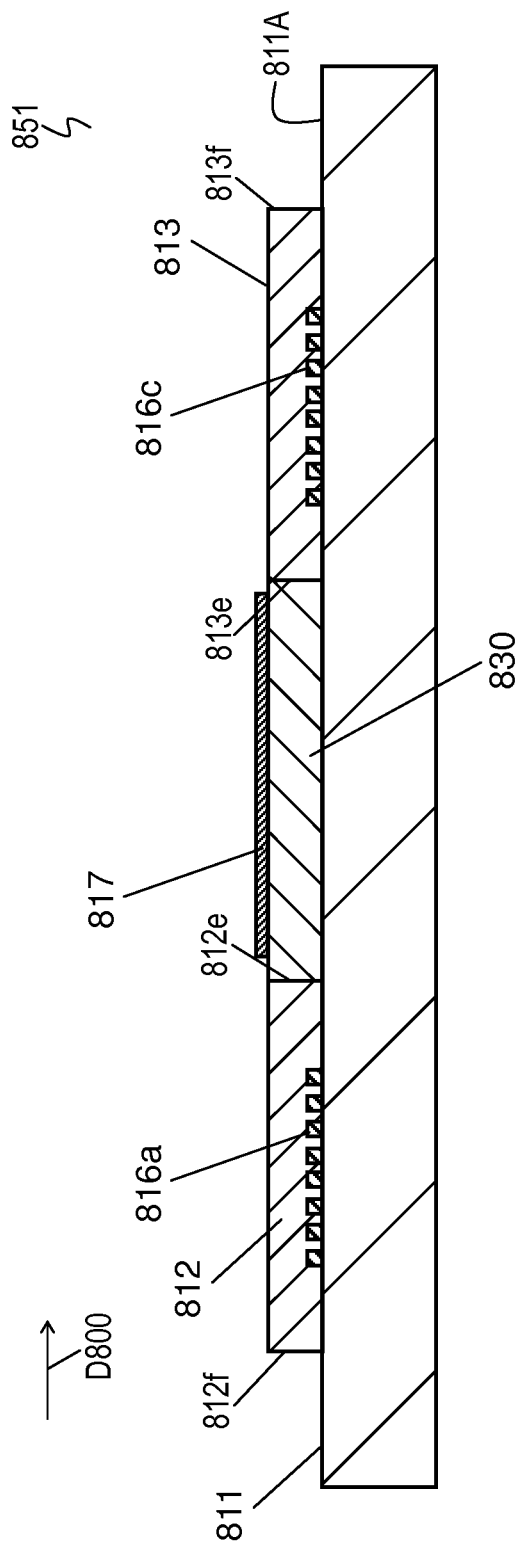
FIG. 18B is a schematic cross-sectional view of the acoustic wave sensor on line 18B-18B shown in FIG. 18A.

FIG. 18A is a schematic top view of acoustic wave sensor 851 according to Exemplary Embodiment 10. FIG. 18B is a schematic cross-sectional view of acoustic wave sensor 851 on line 18B-18B shown in FIG. 18A. In FIGS. 18A and 18B, components identical to those of acoustic wave sensor 800 shown in FIGS. 14A and 14B are denoted by the same reference numerals. Acoustic wave sensor 851 further includes dielectric layer 830 provided between reaction section 817 and piezoelectric substrate 811. Dielectric layer 830 is provided on upper surface 811A of piezoelectric substrate 811. Reaction section 817 is provided on upper surface 830A of dielectric layer 830. Reaction section 817 is located above propagation regions 811P and 811Q. Dielectric layer 830 is located between transmitting electrode cover 812 and receiving electrode cover 813. Dielectric layer 830 is made of dielectric material, such as silicon dioxide. Energy of the acoustic wave can concentrate on reaction section 817 to enhance sensitivity of acoustic wave sensor 851 by appropriately adjusting the thickness of dielectric layer 830 and the thickness of reaction section 817. Acoustic wave sensors 852 to 854 according to Embodiments 7 to 9 may further include a dielectric layer identical to dielectric layer 830, providing the same effects.

Exemplary Embodiment 11

Figure 19A:
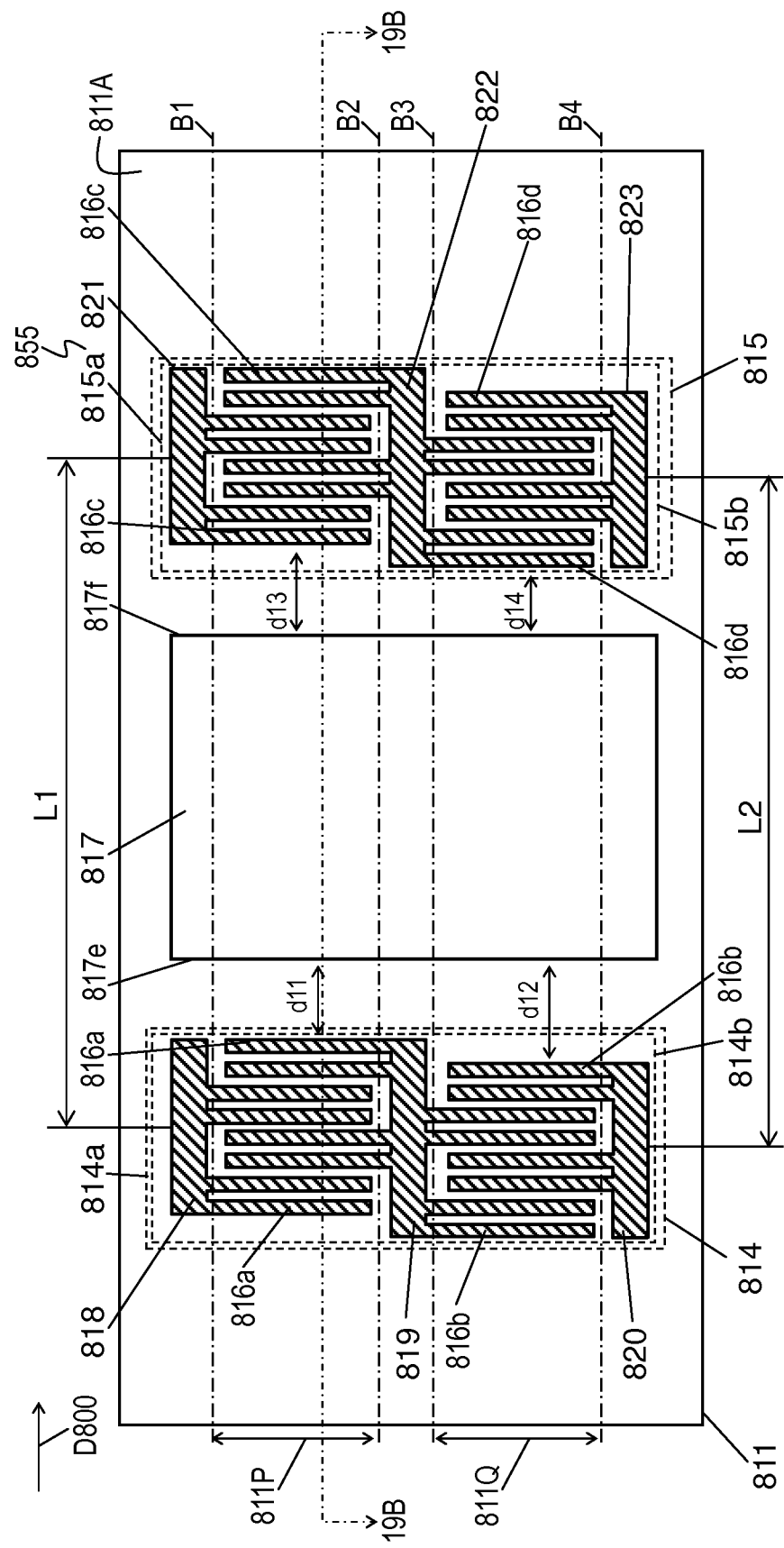
FIG. 19A is a schematic top view of an acoustic wave sensor according to Exemplary Embodiment 11.
Figure 19B:
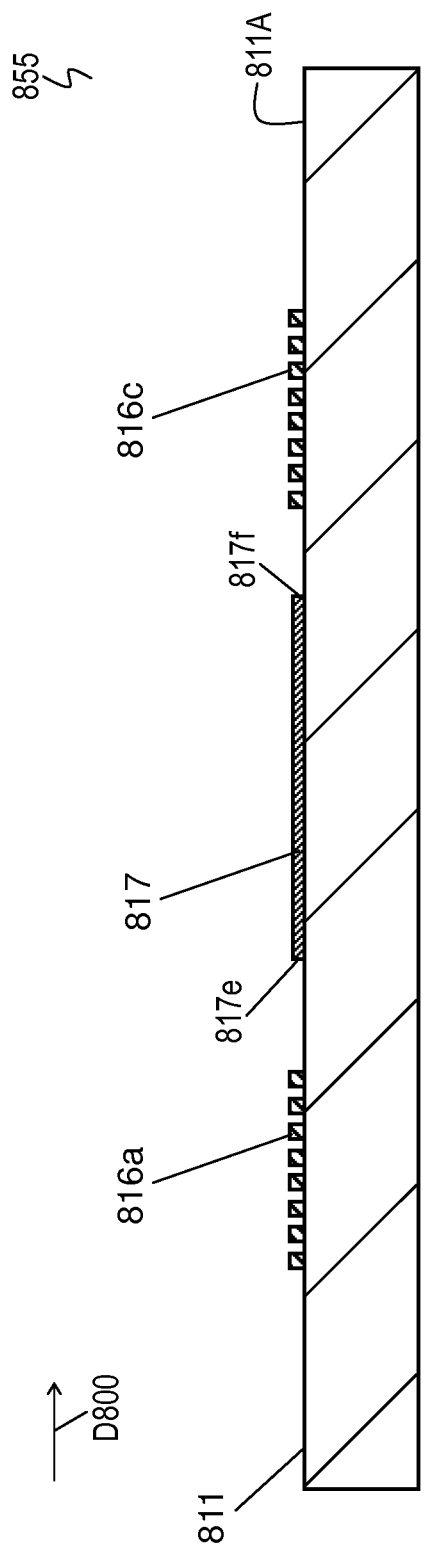
FIG. 19B is a schematic cross-sectional view of the acoustic wave sensor on line 19B-19B shown in FIG. 19A.

FIG. 19A is a schematic top view of acoustic wave sensor 855 according to Exemplary Embodiment 11. FIG. 19B is a schematic cross-sectional view of acoustic wave sensor 855 on line 19B-19B shown in FIG. 19A. In FIGS. 19A and 19B, components identical to those of acoustic wave sensor 800 shown in FIGS. 14A and 14B are denoted by the same reference numerals.

Acoustic wave sensor 855 include none of transmitting electrode cover 812 and receiving electrode cover 813 of acoustic wave sensor 800 according to Embodiment 6. Even if covers 812 and 813 are not included, a difference in acoustic impedance is generated on the end of reaction section 817, hence causing the reflection of the acoustic wave. The distance between each of electrode portions 814 and 815 and respective one of ends of reaction section 817 may be determined similarly to those of acoustic wave sensor 800 according to Embodiment 6, thereby preventing the characteristic of the acoustic wave from being influenced by the reflection.

The configuration of acoustic wave sensor 855 will be described below. Reaction section 817 provided between transmitting electrode portion 814 and receiving electrode portion 815 in propagation direction D800 has end 817e facing transmitting electrode portion 814 and end 817f facing receiving electrode portion 815. Acoustic wave sensor 855 satisfies at least one of a condition that the difference between distance d11 from transmitting electrode 814a to end 817e of reaction section 817 and distance d12 from transmitting electrode 814b to end 817e of reaction section 817 is different from n·λ/2 (λ is the wavelength of the acoustic wave, and n is an integer) and a condition that the difference between distance d13 from receiving electrode 815a to end 817f of reaction section 817 and distance d14 from receiving electrode 815b to end 817f of reaction section 817 is different from m·λ/2 (m is an integer) in propagation direction D800. This configuration can prevent the degradation in the characteristic of the acoustic wave by the reflection. Consequently, acoustic wave sensor 855 prevents the occurrence of ripple on the characteristic, hence having excellent sensor sensitivity and fewer malfunctions.

Acoustic wave sensor 855 satisfies at least one of the condition that the difference between distance d11 and distance d12 is λ/4+n·λ/2 and the condition that the difference between distance d13 and distance d14 is λ/4+m·λ/2 in propagation direction D800. This configuration allows the phase of the acoustic wave which is excited by transmitting electrode 814a, is reflected on the end of reaction section 817, is excited again by transmitting electrode 814a, and propagating to receiving electrode portion 815 to become opposite to the phase of the acoustic wave which is excited by transmitting electrode 814b, is reflected on the end of reaction section 817, is excited again by transmitting electrode 814b, and propagating to receiving electrode portion 815. Accordingly, these acoustic waves are canceled, and prevent the characteristic of the acoustic wave from being influenced by the reflection on end 817e of reaction section 817. Similarly, the phase of some of the acoustic wave propagating from transmitting electrode 814a, is reflected on receiving electrode 815a, is reflected again on end 817e of reaction section 817, and reaching receiving electrode 815a becomes opposite to the phase of some of the acoustic wave propagating from transmitting electrode 814b, is reflected on receiving electrode 815b, is reflected again on end 817f of reaction section 817, and reaching receiving electrode 815b. Accordingly, these acoustic waves are canceled, and the characteristic of the acoustic wave from being influenced by the reflection on end 817f of reaction section 817. Consequently, acoustic wave sensor 855 according to Embodiment 11 prevents the occurrence of ripple on the characteristic, hence having excellent sensor sensitivity and fewer malfunctions.

In the embodiments described above, terms, such as "upper surface" and "above", indicating directions merely indicate a relative direction dependent on only the relative positional relationship of components, such as including the piezoelectric substrate and the insulating film, of the acoustic wave sensor, and do not indicate absolute directions, such as a vertical direction.

INDUSTRIAL APPLICABILITY

An acoustic wave sensor according to the present invention has high detection sensitivity, and is adaptable to electronic devices, such as various medical devices.

REFERENCE MARKS IN THE DRAWINGS

601 Acoustic Wave Sensor
602 Piezoelectric Substrate
602P Propagation Region
603 Transmitting Electrode
604 Receiving Electrode
605 Reaction Section
606 Insulating Film (First Insulating Film)
607 Insulating Film (Second Insulating Film)
701 Acoustic Wave Sensor
702 Piezoelectric Substrate
703 Transmitting Electrode (Electrode)
704 Receiving Electrode (Electrode)
705 Reaction Section
706 Dielectric Film
707 Electrode
708 Concave Portion
709 Convex Portion
710 Antibody
711 Adhesive Layer
711P Corrugate Portion
712 Slit
800 Acoustic Wave Sensor
811 Piezoelectric Substrate
811P Propagation Region (First Propagation Region)
811Q Propagation Region (Second Propagation Region)
812 Transmitting Electrode Cover
813 Receiving Electrode Cover
814 Transmitting Electrode Portion
814a Transmitting Electrode (First Transmitting Electrode)
814b Transmitting Electrode (Second Transmitting Electrode)
815 Receiving Electrode Portion
815a Receiving Electrode (First Receiving Electrode)
815b Receiving Electrode (Second Receiving Electrode)
817 Reaction Section

The invention claimed is:

1. An acoustic wave sensor comprising:
    a piezoelectric substrate having an upper surface;
    a transmitting electrode configured to excite a main acoustic wave propagating through a propagation region of the upper surface of the piezoelectric substrate;
    a receiving electrode configured to receive the propagated main acoustic wave;
    a first insulating film provided on the propagation region of the upper surface of the piezoelectric substrate;
    a second insulating film contacting the upper surface of the piezoelectric substrate and an upper surface of the first insulating film to cover the first insulating film; and
    a reaction section provided on an upper surface of the second insulating film above the propagation region, the reaction section configured to react with an object,
    wherein a velocity of a transverse wave propagating through the first insulating film is higher than a velocity of a transverse wave propagating through the second insulating film.

2. The acoustic wave sensor according to claim 1, wherein a velocity of the transverse wave propagating through the first insulating film is higher than a velocity of the transverse wave propagating through the piezoelectric substrate.

3. The acoustic wave sensor according to claim 1, wherein a velocity of the transverse wave propagating through the second insulating film is lower than a velocity of the transverse wave propagating through the piezoelectric substrate.

4. The acoustic wave sensor according to claim 1,
    wherein the second insulating film is made of silicon oxide, and
    wherein the first insulating film is made of silicon nitride.

5. The acoustic wave sensor according to claim 1, wherein an end of the first insulating film is located apart from an end of the reaction section and inside the reaction section in a propagation direction in which the main acoustic wave propagates.

6. An acoustic wave sensor comprising:
a piezoelectric substrate having an upper surface;
a transmitting electrode configured to excite a main acoustic wave propagating through a propagation region of the upper surface of the piezoelectric substrate;
a receiving electrode configured to receive the propagated main acoustic wave;
a first insulating film provided on the propagation region of the upper surface of the piezoelectric substrate;
a second insulating film provided on the upper surface of the piezoelectric substrate to cover the first insulating film; and
a reaction section provided on the upper surface of the second insulating film above the propagation region, the reaction section configured to react with an object,
wherein a velocity of a transverse wave propagating through the first insulating film is higher than a velocity of a transverse wave propagating through the second insulating film
wherein the first insulating film has:
- a first end facing the transmitting electrode in a propagation direction in which the main acoustic wave propagates;
- a second end facing the receiving electrode in the propagation direction; and
- a center part provided between the transmitting electrode and the receiving electrode in the propagation direction, and
wherein a thickness of the center part of the first insulating film is larger than a thickness of the first end or a thickness of the second end of the first insulating film.

7. The acoustic wave sensor according to claim 6, wherein the first end of the first insulating film has a tapered shape having a thickness decreases toward the transmitting electrode.

8. The acoustic wave sensor according to claim 6, wherein the second end of the first insulating film has a tapered shape having a thickness decreases toward the receiving electrode.

9. The acoustic wave sensor according to claim 7, wherein the second end of the first insulating film has a tapered shape having a thickness decreases toward the receiving electrode.

10. The acoustic wave sensor according to claim 6, wherein a velocity of the transverse wave propagating through the first insulating film is higher than a velocity of the transverse wave propagating through the piezoelectric substrate.

11. The acoustic wave sensor according to claim 6, wherein a velocity of the transverse wave propagating through the second insulating film is lower than a velocity of the transverse wave propagating through the piezoelectric substrate.

12. The acoustic wave sensor according to claim 6,
wherein the second insulating film is made of silicon oxide, and
wherein the first insulating film is made of silicon nitride.

13. The acoustic wave sensor according to claim 6, wherein an end of the first insulating film is located apart from an end of the reaction section and inside the reaction section in a propagation direction in which the main acoustic wave propagates.

* * * * *